(12) United States Patent
Sugiki et al.

(10) Patent No.: US 8,096,976 B2
(45) Date of Patent: Jan. 17, 2012

(54) VALVE BODY AND MEDICAL TOOL

(75) Inventors: Tsutomu Sugiki, Nakakoma-gun (JP); Masaaki Kasai, Nakakoma-gun (JP); Yukio Imai, Nakakoma-gun (JP); Shingo Ishii, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/732,535

(22) Filed: Mar. 26, 2010

(65) Prior Publication Data

US 2010/0185153 A1 Jul. 22, 2010

Related U.S. Application Data

(63) Continuation of application No. PCT/JP2008/067328, filed on Sep. 25, 2008.

(30) Foreign Application Priority Data

Sep. 27, 2007 (JP) ................................. 2007-252477
Sep. 27, 2007 (JP) ................................. 2007-252478

(51) Int. Cl.
*A61M 5/178* (2006.01)
(52) U.S. Cl. .................................................. 604/167.04
(58) Field of Classification Search ............. 604/167.01, 604/167.02, 167.04, 167.06, 247, 256; 251/149.1
See application file for complete search history.

(56) References Cited

U.S. PATENT DOCUMENTS

4,610,665 A * 9/1986 Matsumoto et al. ..... 604/167.04
(Continued)

FOREIGN PATENT DOCUMENTS

EP 2213327 A1 * 8/2010
(Continued)

OTHER PUBLICATIONS

*International Search Report issued by the Japanese Patent Office on Jan. 13, 2009 as the International Searching Authority in International Application No. PCT/JP2008/067328.

*Primary Examiner* — Nicholas Lucchesi
*Assistant Examiner* — Aarti B Berdichevsky
(74) *Attorney, Agent, or Firm* — Buchanan Ingersoll & Rooney PC

(57) ABSTRACT

A valve body is formed from an elastic member in the form of an elliptic or circular film (disk shape) having an upper face and a lower face. The valve body has an opening and closing section which is opened and closed in response to insertion and pulling out of a dilator and is formed from a first slit, a second slit, a second concave portion and two third concave portions. A pair of ribs and six projections are formed on the lower face side of the valve body. The ribs are disposed in opposing relationship to each other with the second slit interposed therebetween and extend along the lower face. Further, the projections are disposed such that they are positioned on the inner side of the ribs and are opposed to each other with the second slit interposed therebetween.

23 Claims, 16 Drawing Sheets

U.S. PATENT DOCUMENTS

| | | | |
|---|---|---|---|
| 4,895,565 A | 1/1990 | Hillstead | |
| 5,114,408 A * | 5/1992 | Fleischhaker et al. | ... 604/167.04 |
| 5,149,327 A | 9/1992 | Oshiyama | |
| 5,273,546 A * | 12/1993 | McLaughlin et al. | ... 604/167.04 |
| 5,312,363 A | 5/1994 | Ryan et al. | |
| 5,496,289 A | 3/1996 | Wenstrom, Jr. | |
| 6,632,200 B2 * | 10/2003 | Guo et al. | ...... 604/247 |
| 2001/0041872 A1 | 11/2001 | Paul, Jr. | |
| 2002/0010425 A1 * | 1/2002 | Guo et al. | ......... 604/167.04 |
| 2004/0094734 A1 * | 5/2004 | Funari et al. | ............. 251/40 |
| 2005/0192537 A1 | 9/2005 | Osborne et al. | |
| 2008/0033363 A1 * | 2/2008 | Haberland et al. | ....... 604/167.03 |

FOREIGN PATENT DOCUMENTS

| | | |
|---|---|---|
| EP | 2213328 A1 * | 8/2010 |
| JP | 59-133877 A | 8/1984 |
| JP | 5-4843 Y2 | 2/1993 |
| JP | 6-039011 U | 5/1994 |
| JP | 2510887 B2 | 6/1996 |
| JP | 2003-522545 T | 7/2003 |
| JP | 2004-154456 A | 6/2004 |
| JP | 3547278 B2 | 7/2007 |
| WO | WO 2006/086711 A1 | 8/2006 |

* cited by examiner

VALVE BODY AND MEDICAL TOOL

This application is a continuation of International Application No. PCT/JP2008/067328 filed on Sep. 25, 2008, and claims priority to Japanese Application No. 2007-252478 filed on Sep. 27, 2007 and Japanese Application No. 2007-252477 filed on Sep. 27, 2007, the entire content of all three of which is incorporated herein by reference.

TECHNICAL FIELD

This invention generally relates to a valve body. More specifically, the invention pertains to a valve body used in a medical tool, and a medical tool which incorporates the valve body, wherein the valve body includes an opening and closing section which is opened and closed in response to insertion and pulling off of an elongated medical member such as, for example, a catheter, a guide wire or a dilator.

BACKGROUND DISCUSSION

When an elongated member used for medical care, such as a catheter or a guide wire, is to be introduced into a living organism, an introducer (medical tool) is used. An example of one such introducer is disclosed in Japanese Patent Publication No. Hei 2-949.

This introducer is composed of a hub having a tubular shape, a sheath having a cap mounted at one end portion of the hub and a sheath tube connected to the other end portion of the hub, and a dilator which is inserted into and used together with the sheath in order to facilitate introduction of the sheath into a living organism. An opening is provided in the cap such that it is communicated with a hollow portion of the hub. A valve body having a disk shape covers the opening to maintain a liquid-tight state of the hollow portion of the hub.

The valve body is made of an elastic material such as silicone rubber and has two slits formed thereon that intersect crosswise with each other. The slits are placed into an open state when an elongated member (pipe body) is inserted into the sheath, but are placed into a closed state when the elongated member is pulled off from the sheath.

However, with such a valve body as just described, if an elongated member is kept inserted for a long period of time or insertion and pulling off of an elongated member are repeated frequently, a tear may occur with the slits, and there is the possibility that the tear may further advance.

If a tear occurs with the slits, when the elongated medical member is pulled off and the slits are closed, the liquid-tightness of the valve body (slits) may be deteriorated (damaged) by the tear. This may also be the case even when the elongated member is positioned in the valve body.

Further, even if a tear does not occur, for example, when coagulations or the like of the blood stick in the sheath are sucked and removed through the side port, since the inside of the sheath is placed into a negative pressure state, there is the possibility that a central portion of the valve body may be drawn into the inside of the sheath to open the slits thereby to allow air to be sucked into the inside of the sheath from the outside.

In this manner, the prior art valve body described above is not fully satisfactory with respect to sealability (sealing performance).

SUMMARY

A valve body and a medical tool embodying the valve body are disclosed which allow insertion and pulling off of an elongated member to be readily carried out while possessing superior sealability.

A valve body having upper and lower faces is made of an elastic material and has an opening and closing section which opens and closes in response to insertion and pulling out of an elongated member into and from the valve body. The opening and closing section includes a first slit extending to the upper face but not to the lower face, and a second slit extending to the lower face but not to the upper face and intersecting with the first slit in the inside of the valve body. The valve body further includes a pair of ribs on the lower face side. The ribs are disposed in opposing relationship to each other with the second slit interposed therebetween and extending along the lower face. In addition, projections are provided between the pair of ribs and the second slit.

This configuration of the valve body improves the sliding performance of the elongated member, insertion and pulling out of the elongated member can be carried out quite readily, and the sealability (sealing performance) of the opening and closing section is improved.

In particular, the valve body is reinforced by the ribs, and, for example, the ribs contact a mounting section for the valve body to suppress deformation of the valve body, whereby the sealing performance of the opening and closing section is improved.

The valve body is also reinforced by the projections, and consequently, deformation of the valve body is suppressed and the sealability of the opening and closing section is improved.

When the elongated member is pulled out from the valve body (opening and closing section), the valve body is deformed such that a central portion of the valve body is displaced in the direction of the movement of the elongated member and the projections contact (point-contact) an outer circumferential surface of the elongated member. Consequently, the contact area of the outer circumferential surface of the elongated member and the valve body decreases, and the resistance (sliding resistance) when the elongated member is pulled out from the valve body decreases. Consequently, the sliding performance of the elongated member is improved, and the elongated member can be relatively readily pulled out from the valve body.

Therefore, the valve body disclosed here has useful application in a sheath of an introducer for introducing an elongated medical member for use with medical care, such as for example a catheter or a guide wire, into a living organism.

Preferably, the ribs have an arcuate shape.

With this configuration, when the valve body is mounted on a tubular mounting section, the outer side of the ribs can contact the mounting section, and consequently, it is possible to inhibit or prevent the second slit from being opened, and so the sealability of the opening and closing section can be maintained.

In the embodiment of the valve body disclosed here, when the valve body is mounted on a mounting section, the outer side or outer surface of the ribs contacts the mounting section.

According to this configuration, it is possible to inhibit or prevent the second slit from being opened, and so the sealability of the opening and closing section can be maintained.

In the embodiment of the valve body disclosed here, the second slit preferably has a straight line shape as viewed in plan, and the ribs are disposed so as to be line-symmetrical with respect to the second slit and point-symmetrical with respect to an intersecting portion of the first slit and the second slit as viewed in plan.

It is thus possible to inhibit or prevent the second slit from being opened with a higher degree of certainty, and so the sealability of the opening and closing section can be maintained.

In the embodiment of the valve body disclosed here, the ribs are preferably not provided on an extension line of the second slit as viewed in plan.

Thus, when the valve body is deformed, a relief corresponding to the deformed portion is relatively assured. Consequently, the valve body can contact (closely contact) uniformly with the mounting section.

In the embodiment of the valve body disclosed here, the projections are radially disposed with respect to an intersecting portion of the first slit and the second slit.

When the elongated member is moved upwardly and pulled out from the valve body, the valve body is deformed such that a portion thereof in the proximity of the intersecting portion is displaced upwardly and the projections contact (point-contact) with the outer circumferential face of the elongated member. Consequently, the contact area of the outer circumferential face of the elongated member and the valve body decreases, and the sliding resistance when the elongated member is pulled out from the valve body decreases. Consequently, the sliding performance of the elongated member is improved, and the elongated member can be pulled out from the valve body readily.

Preferably, in the embodiment of the valve body disclosed here, the projections extend from the ribs to an intersecting portion of the first slit and the second slit as viewed in plan.

With this configuration, when the elongated member is moved upwardly and pulled out from the valve body, the projections contact (point-contact) the outer circumferential face of the elongated member with a higher degree of certainty. Consequently, the contact area of the outer circumferential face of the elongated member and the valve body decreases, and the sliding resistance when the elongated member is pulled out from the valve body decreases. Consequently, the sliding performance of the elongated member is improved, and the elongated member can be pulled out from the valve body relatively readily.

In the embodiment of the valve body disclosed here, the projections preferably do not extend to the second slit.

Thus, when the elongated member is moved downwardly and inserted into the valve body, the valve body becomes liable to be curved such that a portion thereof in the proximity of the intersecting portion is displaced downwardly by a suitable amount as viewed in plan.

Preferably, all of the gap distances between the ends of the projections on the second slit side and an intersecting portion of the first slit and the second slit are equal to each other.

With this arrangement, when the elongated member is moved upwardly and pulled off from the valve body, the projections and the outer circumferential face of the elongated member can contact uniformly with each other. Consequently, the elongated member can be pulled out from the valve body readily and stably.

In the embodiment of the valve body disclosed here, the second slit has a straight line shape as viewed in plan, and the projections are disposed so as to be line-symmetrical with respect to the second slit and point-symmetrical with respect to an intersecting portion of the first slit and the second slit as viewed in plan.

When the elongated member is moved upwardly and pulled out from the valve body, the valve body is deformed such that a portion thereof in the proximity of the intersecting portion is displaced upwardly and the projections contact (point-contact) with the outer circumferential face of the elongated member. Consequently, the contact area of the outer circumferential face of the elongated member and the valve body decreases, and the sliding resistance when the elongated member is pulled out from the valve body decreases. Consequently, the sliding performance of the elongated member is improved, and the elongated member can be pulled out from the valve body readily.

In the embodiment of the valve body disclosed here, the projections are preferably not provided on an extension line of the second slit as viewed in plan.

With this arrangement, the sliding resistance when the elongated member is moved (inserted and pulled out) with respect to the valve body can be inhibited or prevented from increasing unnecessarily. Consequently, the sliding performance of the elongated member is improved, and insertion and pulling out of the elongated member can be carried out readily.

Preferably, in the valve body disclosed here, the projections have a height which gradually decreases from the rib side toward the second slit side.

Accordingly, when the elongated member is moved downwardly and inserted into the valve body, the sliding resistance can be reduced to a comparatively low value.

In the embodiment of the valve body disclosed here, the projections preferably have a width which gradually decreases from the rib side toward the second slit side.

Thus, when the elongated member is moved downwardly and inserted into the valve body, increase of the sliding resistance of the same can be suppressed.

The projection preferably has a height which is lower than that of the ribs.

With this arrangement, the increasing amount of the volume of the valve body can be suppressed to a comparatively small amount, and the sliding resistance when the elongated member is moved (inserted and pulled off) with respect to the valve body can be set to a comparatively low value.

In the natural state of the valve body, the first slit is open, and the valve body is deformed, when the valve body is mounted on the mounting section, in such a manner as to be compressed toward the intersecting portion of the first slit and the second slit, and the first slit is closed thereby.

This helps provide quite good sliding performance and sealing performance.

In the natural state of the valve body disclosed here, the first slit and the second slit are open, and when the valve body is deformed upon being mounted on the mounting section in such a manner as to be compressed toward the intersecting portion of the first slit and the second slit, the first slit is closed.

With this configuration, superior sliding performance and sealing performance can be obtained.

In the state in which the valve body is mounted on the mounting section, at least part of the second slit is open.

This helps facilitate superior sliding performance and sealing performance.

Preferably, in the valve body disclosed here, the first slit has a shape of a straight line as viewed in plan.

This contributes to the first slit being opened and closed readily and with certainty.

In the embodiment of the valve body disclosed here, the second slit has a shape of a straight line as viewed in plan, and the first slit and the second slit intersect crosswise with each other.

Superior sealing performance can thus be obtained, and the opening and closing section can be opened and closed readily and with certainty.

The elongated medical member can be a dilator, a catheter or a guide wire.

The configuration of the valve body allows insertion and pulling out of the dilator, the catheter or the guide wire to be carried out readily.

In the natural state of the valve body, the first slit is open and a first space is formed by an inner face of the first slit while the second slit is open and a second space is formed from an inner face of the second slit, and the first space and the second space communicate with each other through the intersecting portion.

With this configuration, when the valve body wherein the first space and the second space are communicated with each other through the intersecting portion in the natural state is mounted on the mounting section, the first slit and the second slit are compressed (pressed) individually in a closing direction by the mounting section. Therefore, the first slit is placed into a closely contacting (closed) state wherein the inner faces thereof are pressed against each other. However, by the elastic force of the valve body itself (restoring force tending to open the first slit), the close contact is placed to such a degree that occurrence of blocking is suppressed (or prevented). Similarly, also the second slit is placed into a closely contacting state as the inner faces thereof are pressed against each other. However, by the elastic force of the valve body itself (restoring force tending to open the second slit), the close contact is placed to such a degree that occurrence of blocking is suppressed (or prevented).

If radiation sterilization is carried out in this state, then occurrence of excessive (excessively firm) blocking between the inner faces of the first slit or between the inner faces of the second slit is inhibited or prevented with relative certainty. Consequently, when the elongated medical member is inserted into the valve body for the first time after sterilization, the inner faces of the first slit (also the inner faces of the second slit) are exfoliated readily. Consequently, the penetration resistance of them is reduced, and an operation when the elongated member is inserted and pulled off can be carried out readily. Further, when the elongated member is inserted and pulled off, damage to the first slit or the second slit can be prevented with certainty.

When the valve body is in a state in which the valve body is mounted on the mounting section, the valve body is deformed in such a manner as to be compressed at the intersecting portion such that the first slit and/or the second slit are contacted closely at least at inner peripheral faces thereof in the proximity of the intersecting portion with each other so as to be closed.

With this configuration, if radiation sterilization is carried out in the state in which the valve body is mounted on the mounting section, occurrence of excessive (excessively firm) blocking between the inner faces of the first slit or between the inner faces of the second slit is inhibited or prevented with certainty. Consequently, when the elongated medical member is inserted into the valve body for the first time after sterilization, the inner faces of the first slit (also the inner faces of the second slit) are exfoliated readily. Consequently, the penetration resistance of them is reduced, and an operation when the elongated member is inserted and pulled off can be carried out readily. Further, when the elongated member is inserted and pulled out, damage to the first slit or the second slit can be inhibited or prevented with reliability.

In the embodiment of the valve body disclosed here, the first space and the second space preferably have a flattened shape.

According to this configuration, superior sealing performance is obtained, and the opening and closing section can be opened and closed readily and with certainty.

In the embodiment of the valve body disclosed here, the intersecting portion preferably has a shape of a hexahedron in the natural state, and the sum total in length of those eight sides from among the 12 sides forming the hexahedron which are nodal lines formed by intersection of the inner faces of the first slit and the second slit is 1.0 to 6.0 mm.

If the sum total is within such a numeral value range as given above, the elongated member can be inserted into and pulled out from the valve body suitably (smoothly without causing damage to any of the first slit and the second slit) without depending upon the outer diameter of a portion, which is inserted into a living organism, of the elongated member which is normally used (inserted) in a medical tool. Also, the sealing performance of the opening and closing section in the state wherein the elongated member is fitted in the valve body can be maintained appropriately.

The intersecting portion preferably is positioned at a central portion of the valve body as viewed in plan.

Accordingly, when the elongated member is inserted into and pulled out from the valve body, the operation can be carried out stably.

In the embodiment of the valve body disclosed here, the first space and/or the second space have a depth which gradually decreases from the intersecting portion toward a direction away from the intersecting portion.

Thus, when the elongated medical member is inserted into the first slit, the distal end portion of the elongated member is guided so as to be directed to the intersecting portion, and consequently, the insertion operation can be carried out with certainty. Further, the distal end portion of the elongated member is prevented from piercing (penetrating) a portion of the first slit other than the intersecting portion, and further prevented from extending to the second slit. Consequently, damage to the valve body can be inhibited or prevented.

Preferably, in the valve body disclosed here, the first space and/or the second space has a width which gradually decreases toward the intersecting portion.

With this arrangement, when the elongated member is inserted into the first slit, the distal end portion of the elongated member is guided so as to be directed to the intersecting portion, and consequently, the insertion operation can be carried out with relative certainty.

The first slit and the second slit preferably have a shape of a straight line as viewed in plan and intersect crosswise with each other.

Accordingly, a suitable sealing performance is obtained, and the opening and closing section can be opened and closed readily and with relative certainty.

Another aspect of the disclosure here involves a medical tool outfitted with the valve body disclosed here, with the valve body installed such that the upper face of the valve body is exposed to the outer side and the lower face is exposed to the inside of a flow path.

A medical tool outfitted with such valve body facilitates insertion and pulling out of the elongated member.

BRIEF DESCRIPTION OF THE DRAWING FIGURES

Figure 3:
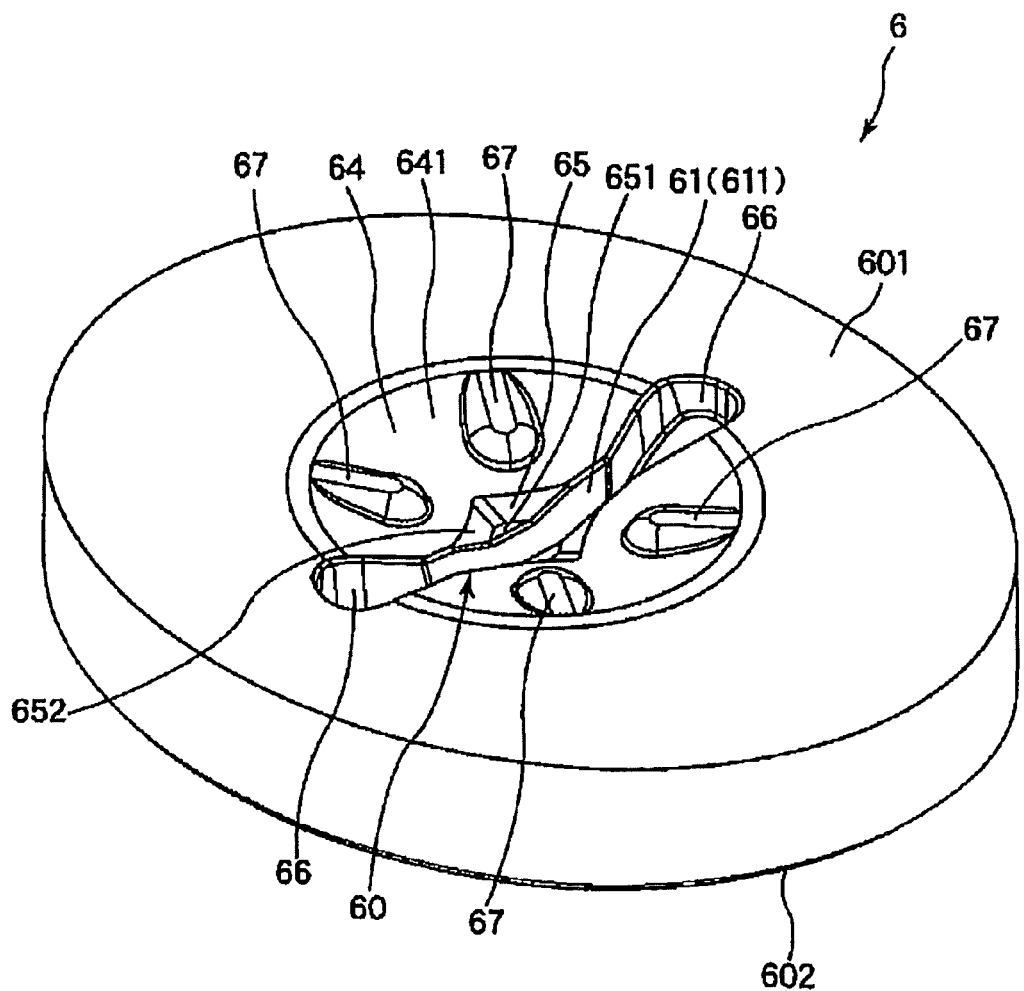
FIG. 3 is an upper perspective view of an embodiment of the valve body disclosed here (the valve body shown in FIGS. 1 and 2) when the valve body in a natural state.
Figure 7:
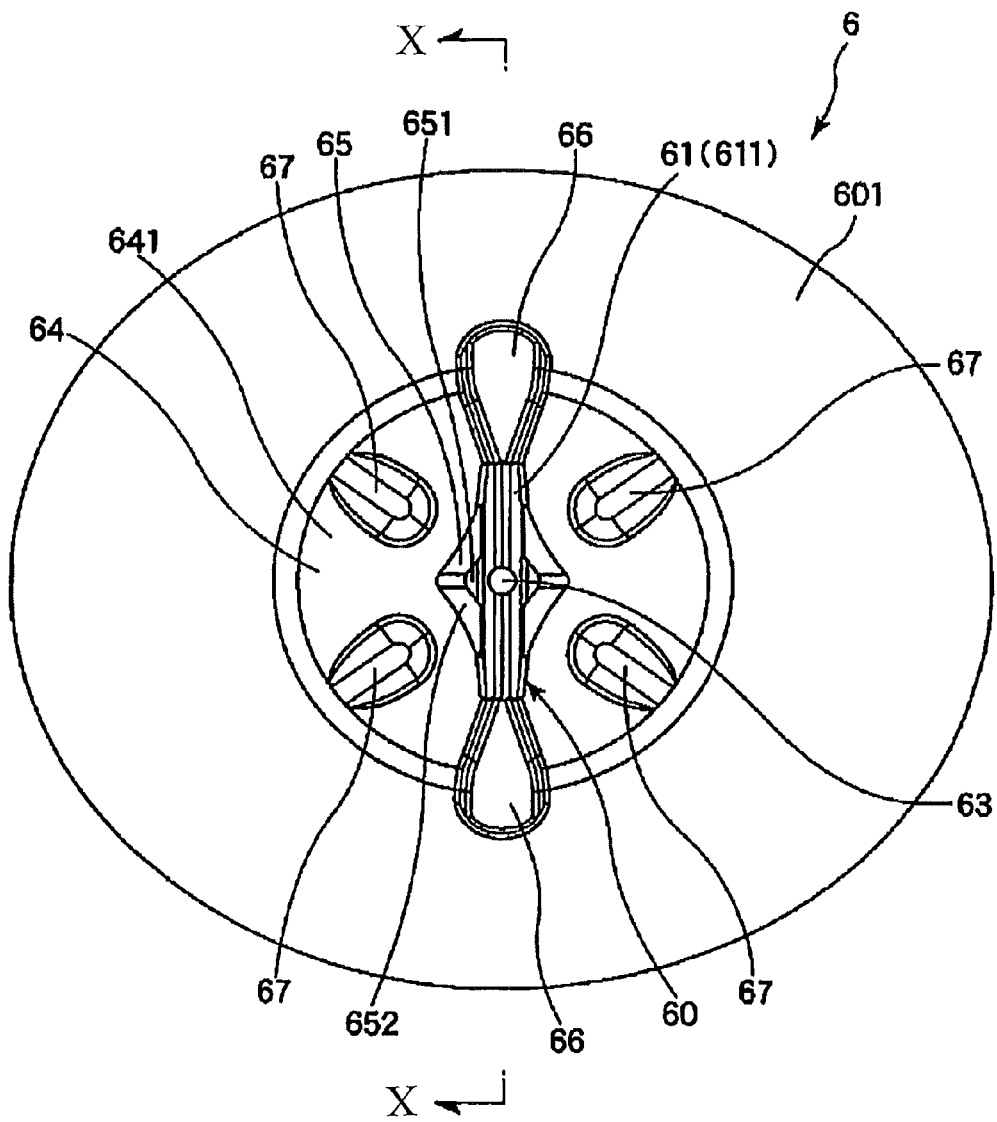
FIG. 7 is a plan view of the valve body (in the natural state) shown in FIG. 3.
Figure 10:
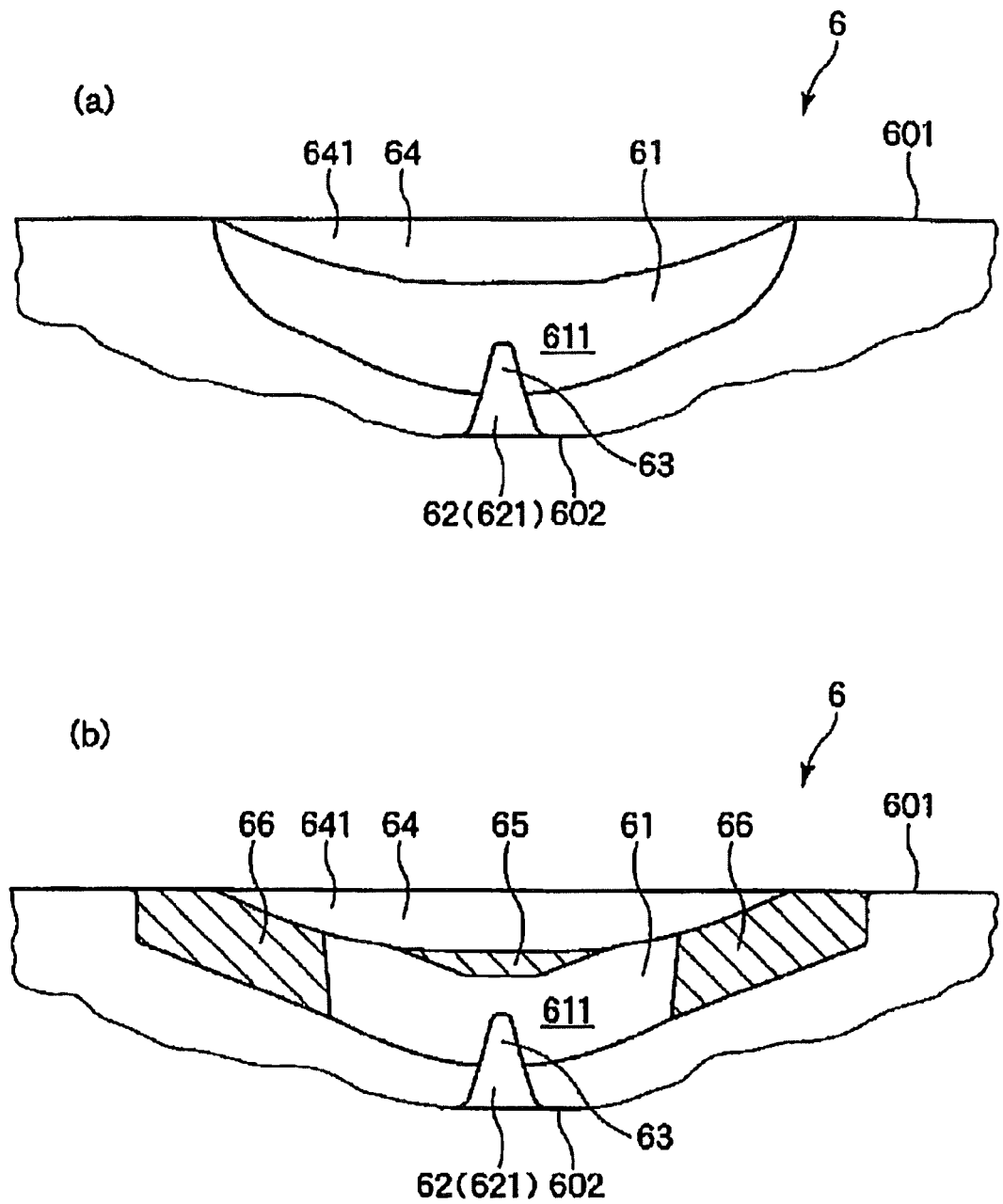

FIGS. 10(a) and 10(b) are views taken along the section line VII-VII in FIG. 7 illustrating the second concave portion and the third concave portion of the valve body (in the natural state) shown in FIG. 3.

Figure 11:
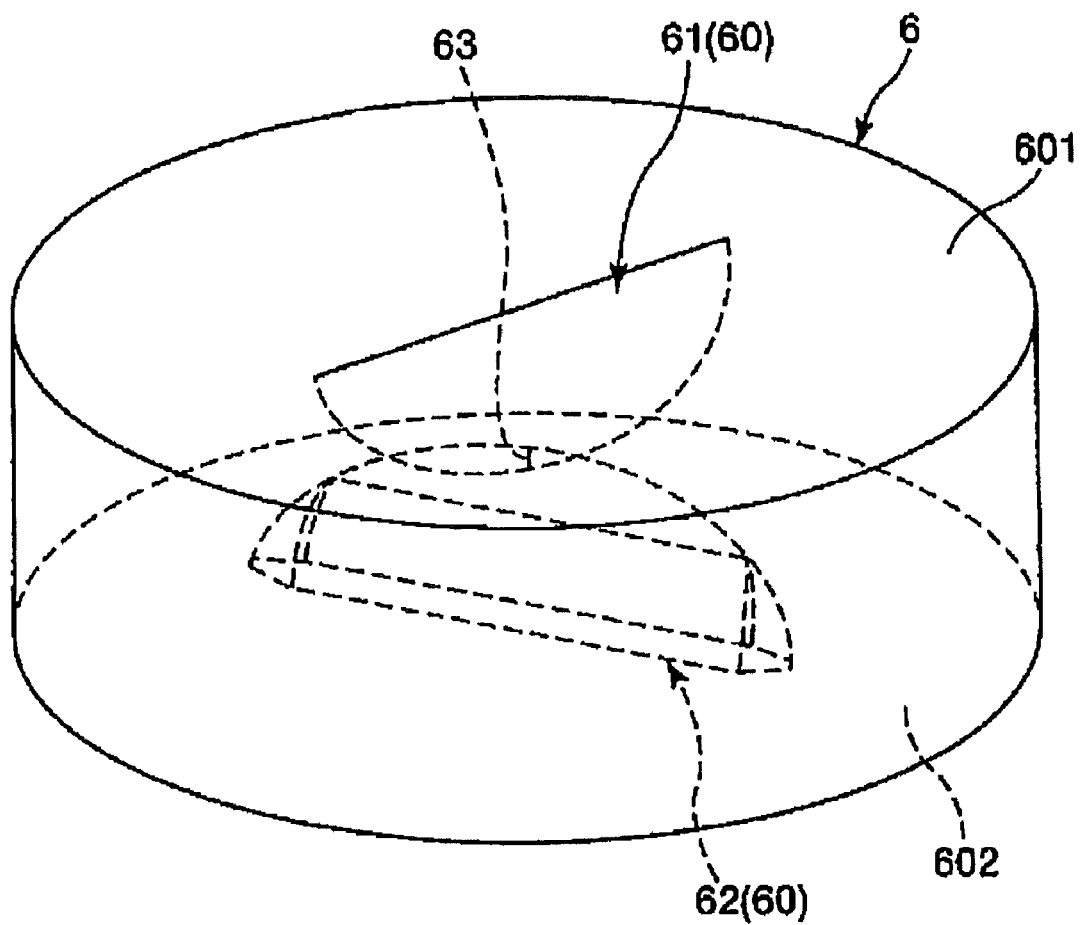

FIG. 11 is a somewhat schematic perspective view of the valve body shown in FIG. 3 in a mounted state.

Figure 12:
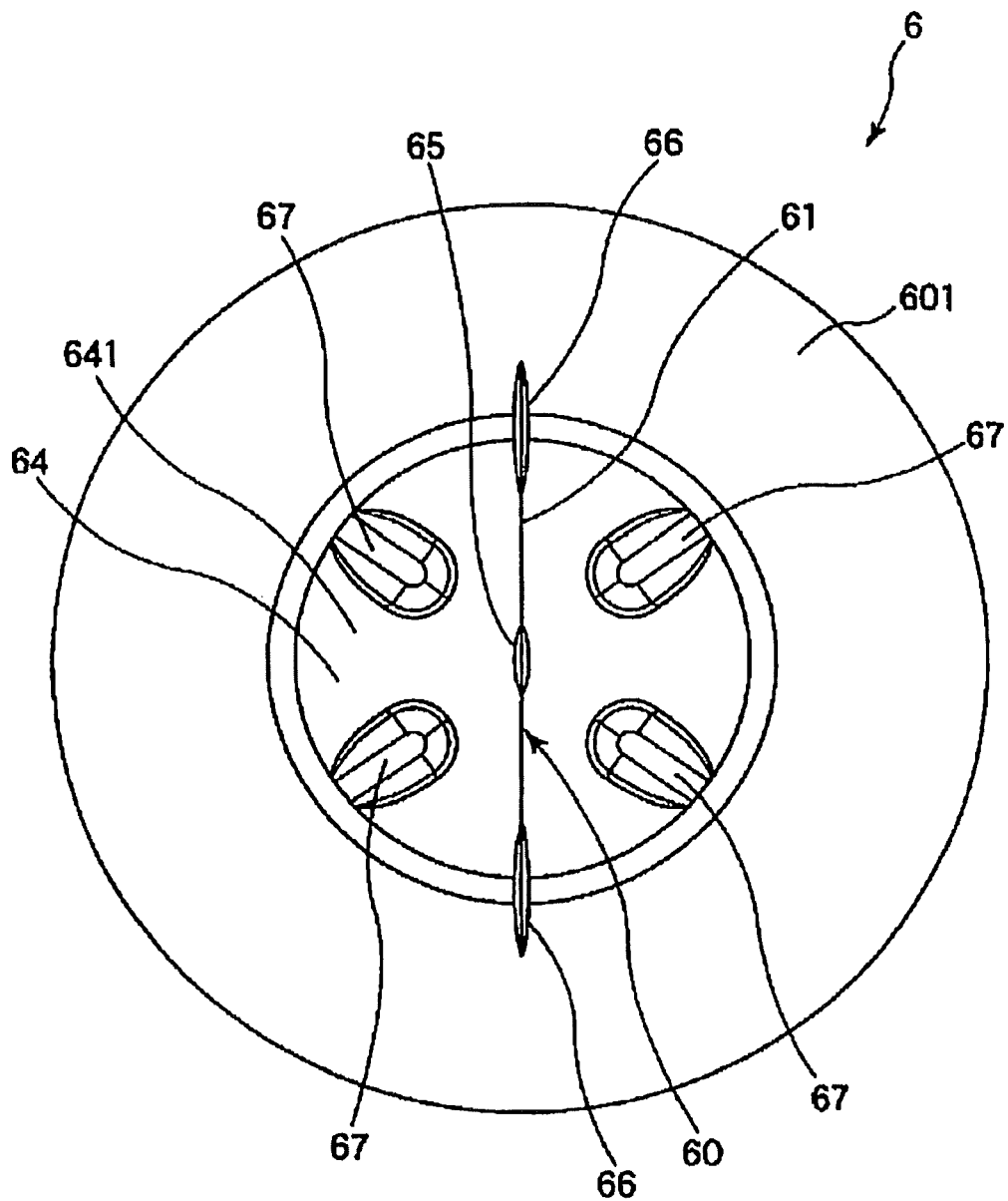

FIG. 12 is a plan view of the valve body shown in FIG. 3 in the mounted state.

Figure 13:
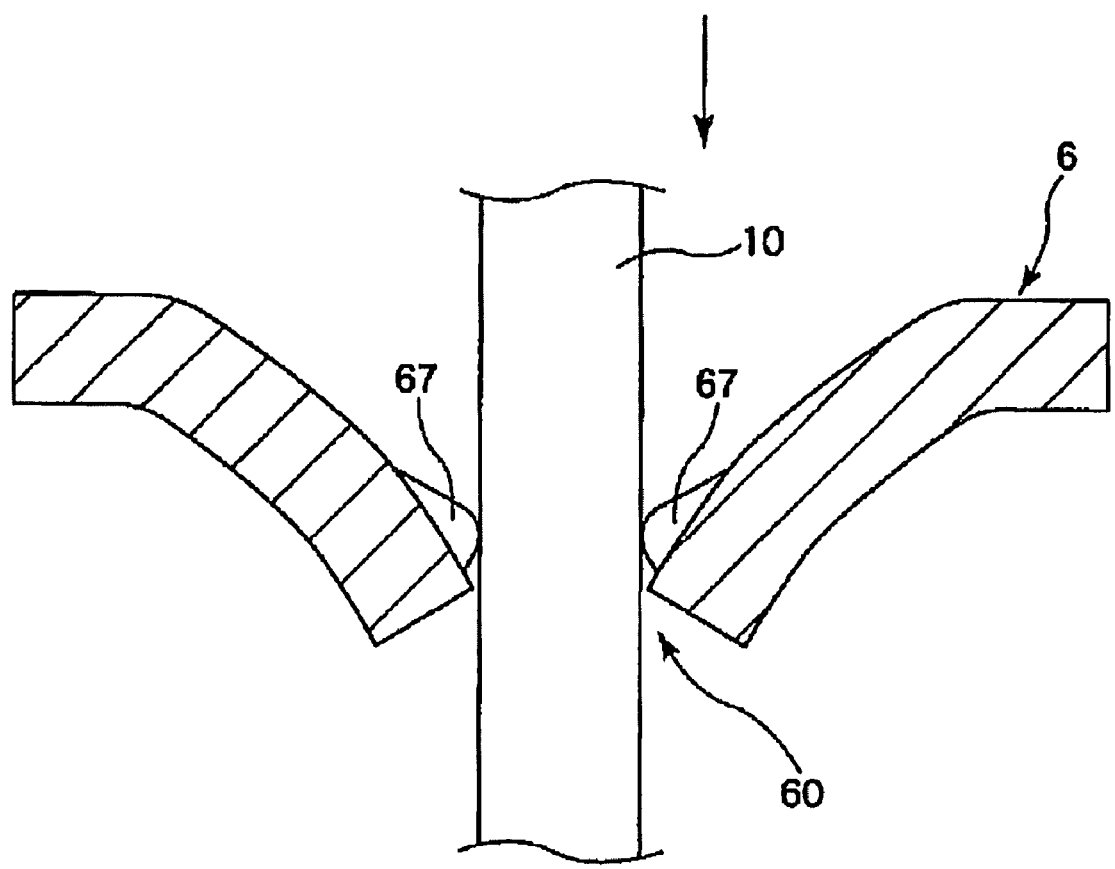

FIG. 13 is a vertical cross-sectional view schematically illustrating a dilator fitted into the valve body when the valve body is in the mounted state shown in FIG. 12.

Figure 14:
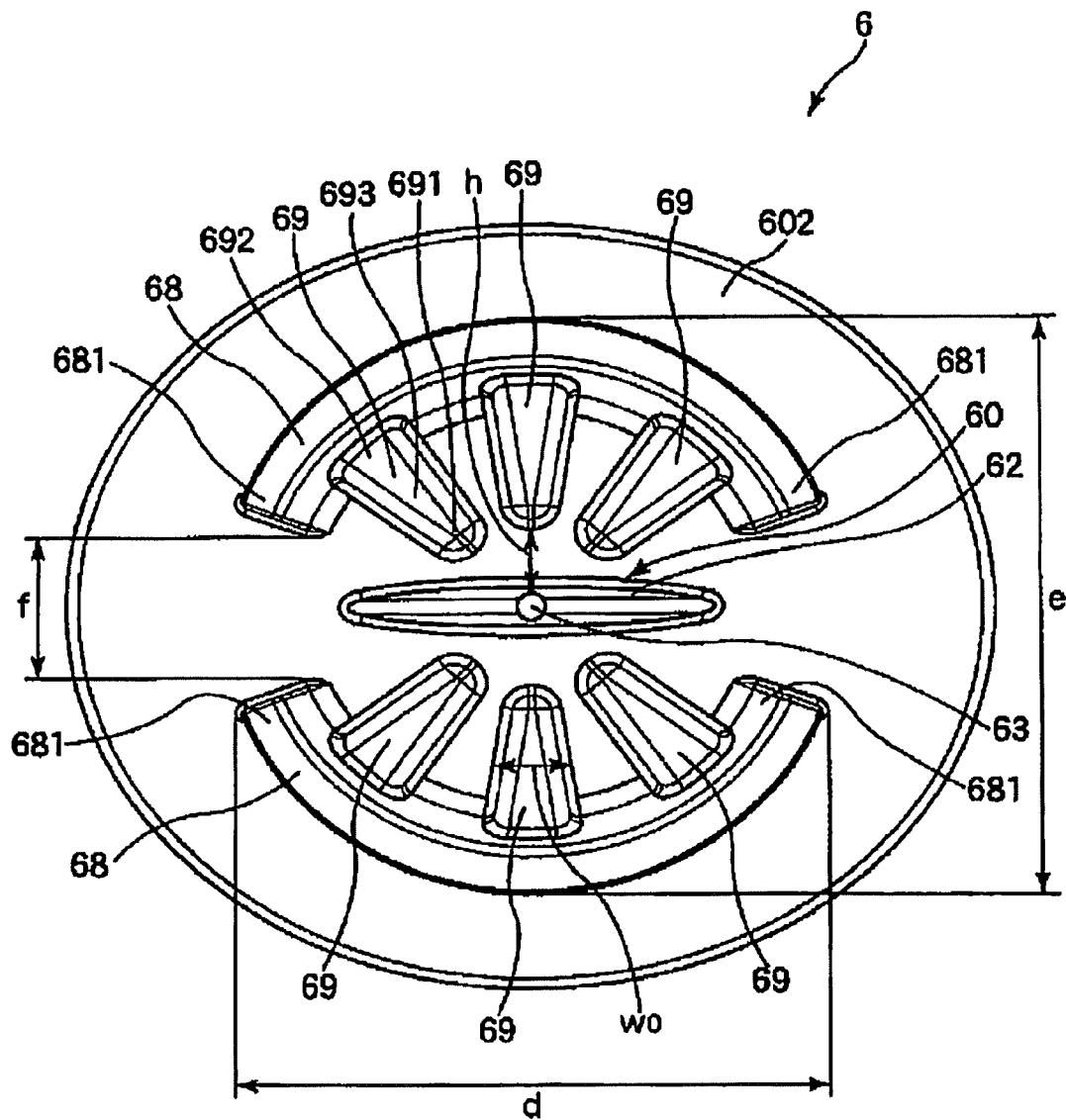

FIG. 14 is a bottom plan view of the valve body (in the natural state) shown in FIG. 3.

Figure 8:
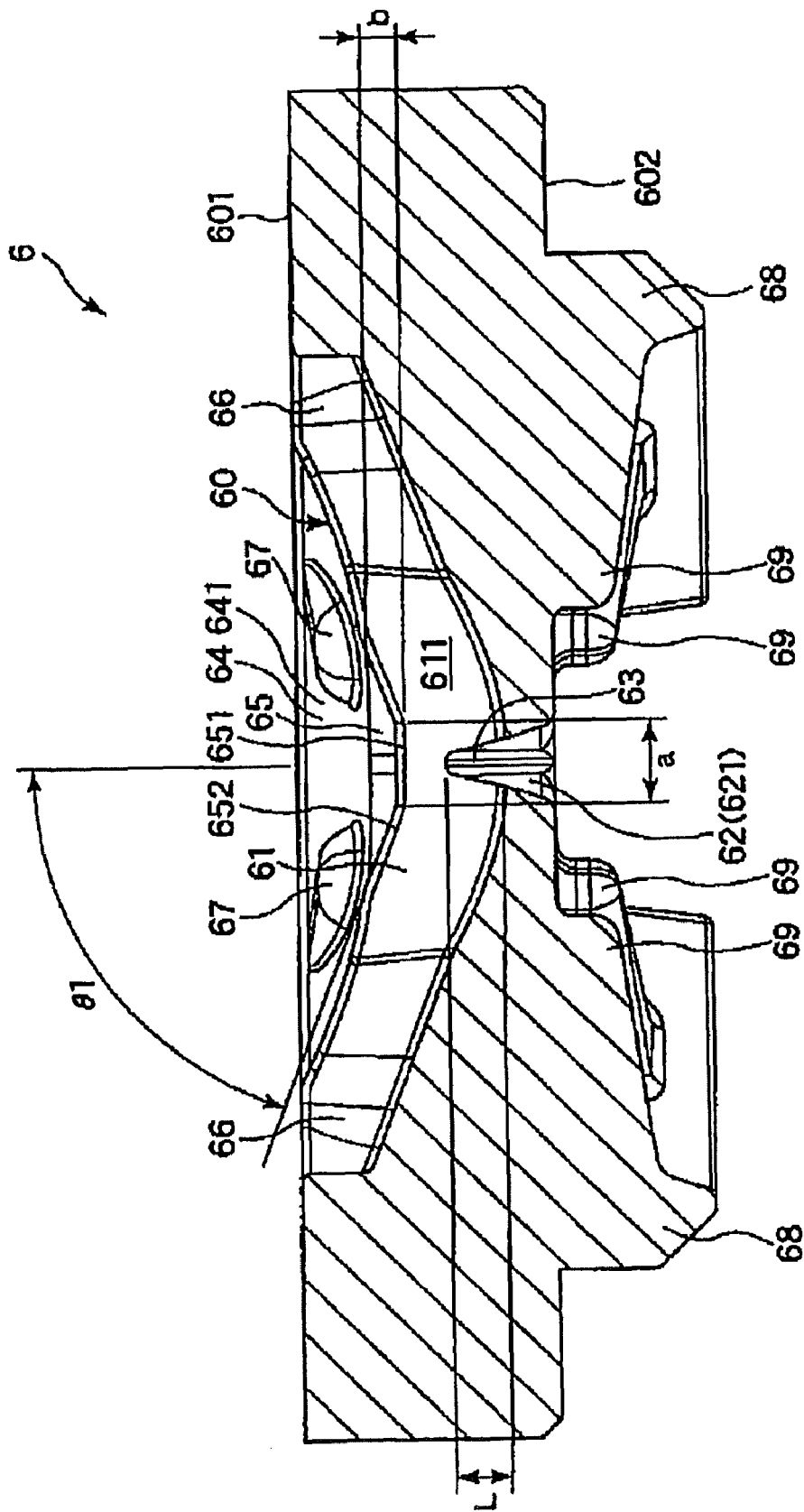
FIG. 8 is a cross-sectional view of the valve body taken along the section line VIII-VIII in FIG. 7.
Figure 15:
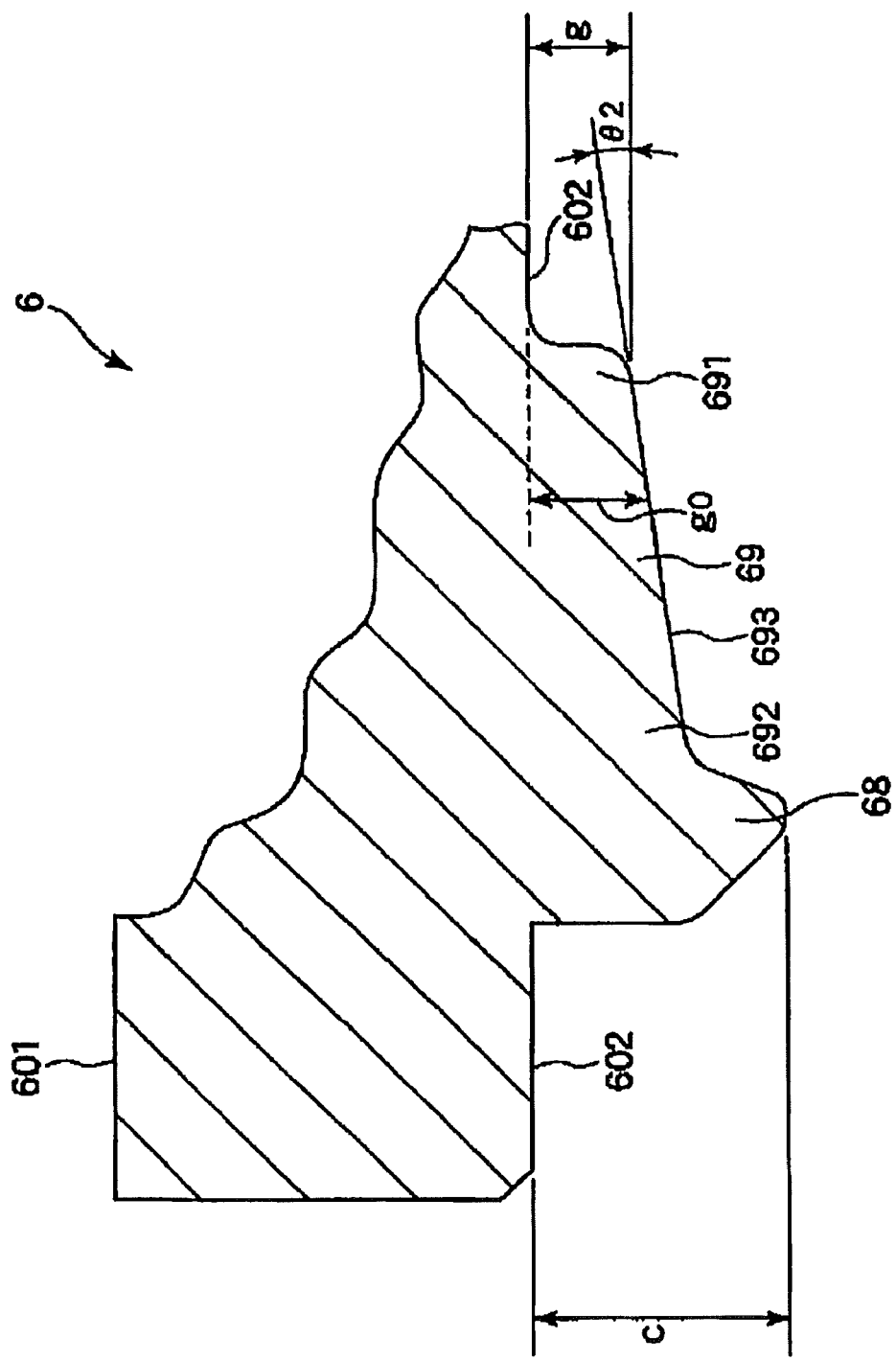

FIG. 15 is a vertical cross-sectional view of a rib and a projection on the lower face side of the valve body in FIG. 8.

Figure 16:
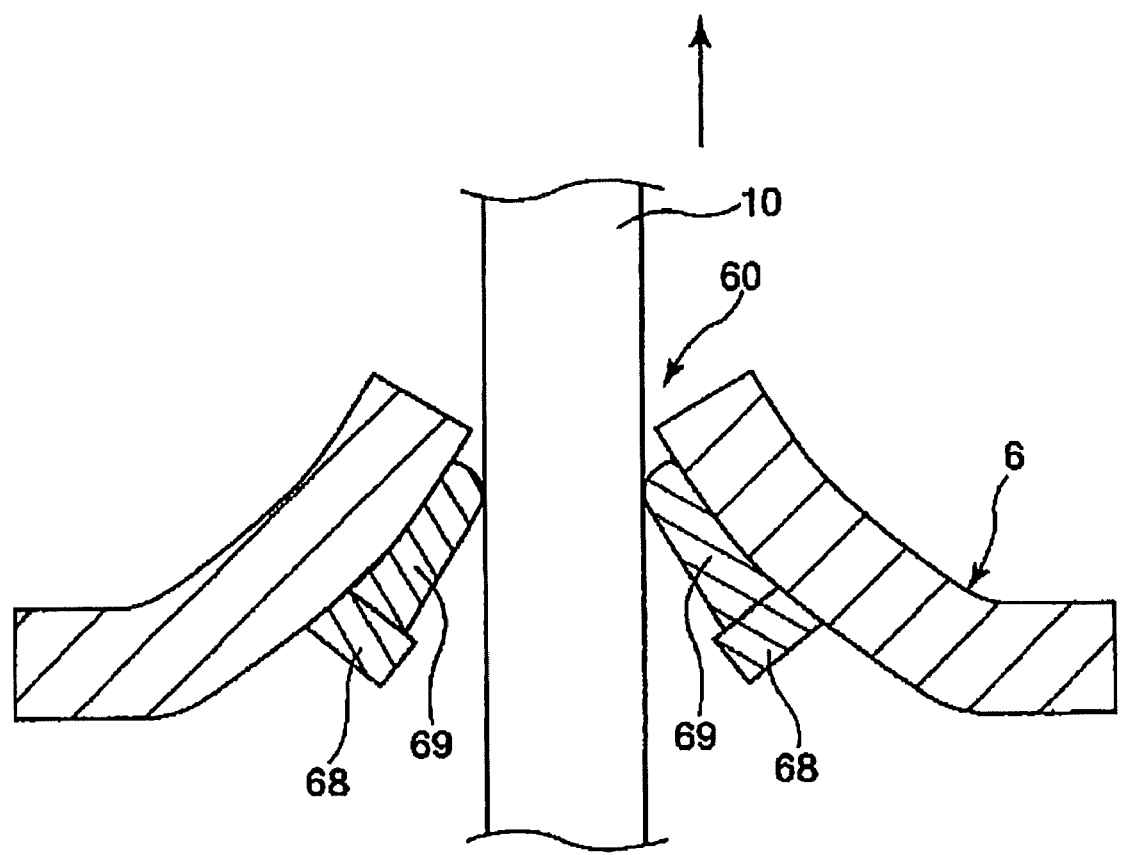

FIG. 16 is a vertical cross-sectional view illustrating the dilator being pulled off (removed) from the valve body when the valve body is in the mounted state shown in FIG. 12.

DETAILED DESCRIPTION

The following describes a valve body and a medical tool disclosed here. In this embodiment disclosed here, the medical tool is, by way of example, an introducer.

Figure 4:
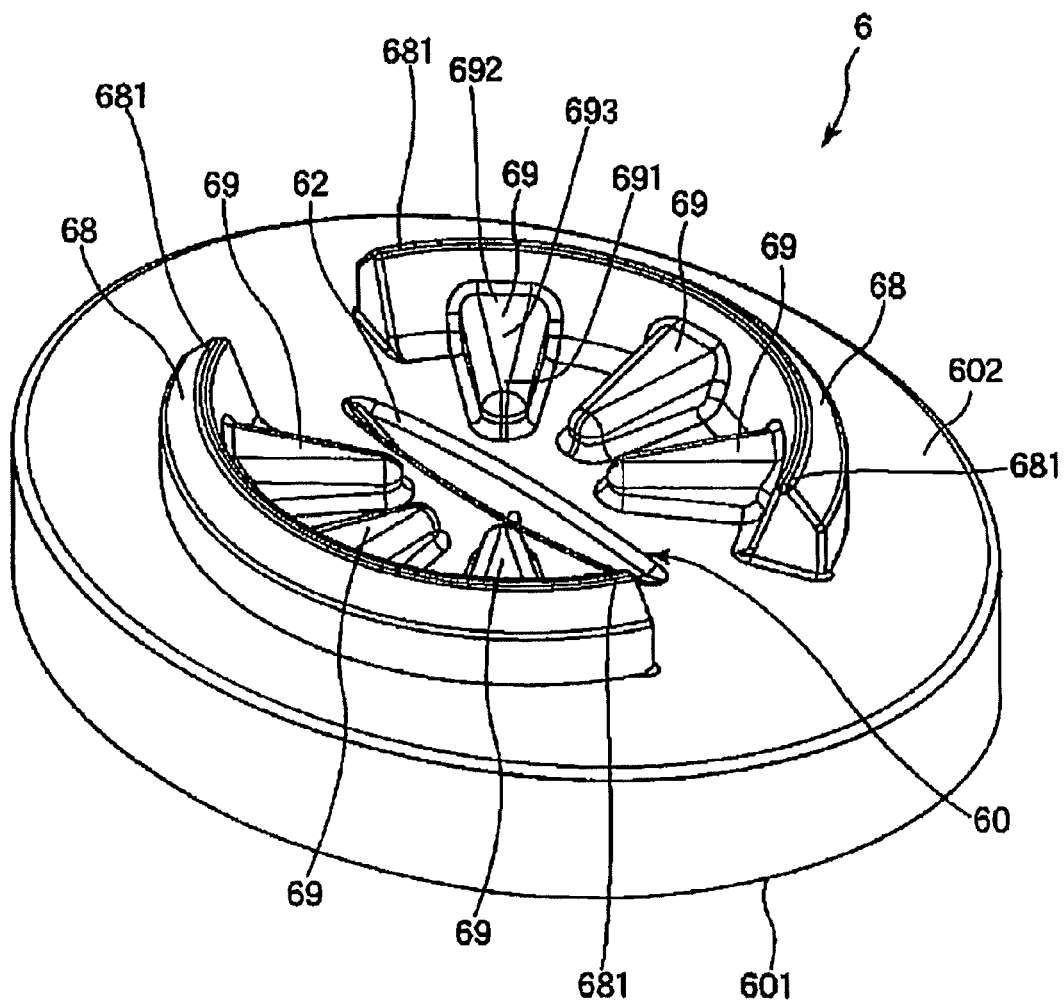
FIG. 4 is a lower perspective view of the valve body (in the natural state) shown in FIG. 3.

In the following description involving FIGS. 1-3, 5, 6, 8, 10, 11, 13, 15 and 16, the upper side is referred to as the "upper" or "proximal end" and the lower side is referred to as the "lower" or "distal end". In FIG. 4, the upper side is referred to as the "lower" or "distal end" and the lower side is referred to as the "upper" or "proximal end". Further, to facilitate illustration and an understanding of the illustrated features, the first slit and the second slit are shown in FIG. 11 with other elements and features omitted.

As mentioned above, the medical tool 1 described and illustrated here by way of example is an introducer 1. The introducer is used to introduce an elongated medical member used in medical care (medical procedure) such as, for example, a guide wire or a catheter into a living organism (for example, a blood vessel or the like).

This introducer 1 is composed of a sheath 7 having a hub 2, a sheath tube (tube) 4 in the form of an elongated pipe having a proximal end secured to the distal end side of the hub 2, sealing means 5 for effecting sealing of the interior of the hub 2 as discussed in more detail below, and a dilator (expanding tube) 10 positioned in and used together with the sheath 7 to facilitate introduction of the sheath 7 into a living organism.

The hub 2 is formed from a hollow pipe body or tubular body.

A side port (connecting portion) 21 extends outwardly away from the outer circumferential portion of the hub 2 so that is projects in a sideward manner (in a sideways direction). The side port 21 is in the form of a tubular member or pipe, and the hollow portion (interior) 211 of the side port 21 communicates with the interior of the hub 2. One end of a preferably flexible tube 8 made of, for example, polyvinyl chloride is connected in a liquid-tight manner to the side port 21.

The sheath tube 4 is a member (portion) to be introduced into a living organism and is formed from a thin pipe-shaped member. The proximal end portion of the sheath tube 4 is secured to the distal end portion of the hub 2 by fitting or another appropriate securing means for securing the sheath tube 4 to the hub 2. Further, the interior of the sheath tube 4 communicates with the interior 211 of the hub 2.

The sealing means 5 for sealing the inside of the hub 2 is provided at a proximal end portion of the hub 2.

The sealing means 5 is composed of a valve body 6 through which the dilator (expanding pipe) 10, a catheter or a guide wire can pass, and an annular (cylindrical) lid member 51 for fixedly supporting the valve body 6 on the hub 2.

The lid member 51 is configured (sized and shaped) such that it can fit into the inner circumferential portion 22 at the proximal end of the hub 2. When the lid member 51 is mounted on the hub 2 with the valve body 6 fixedly supported on the hub 2, the distal end portion of the lid member 51 is positioned in the proximal end inner circumferential portion 22.

Figure 1:
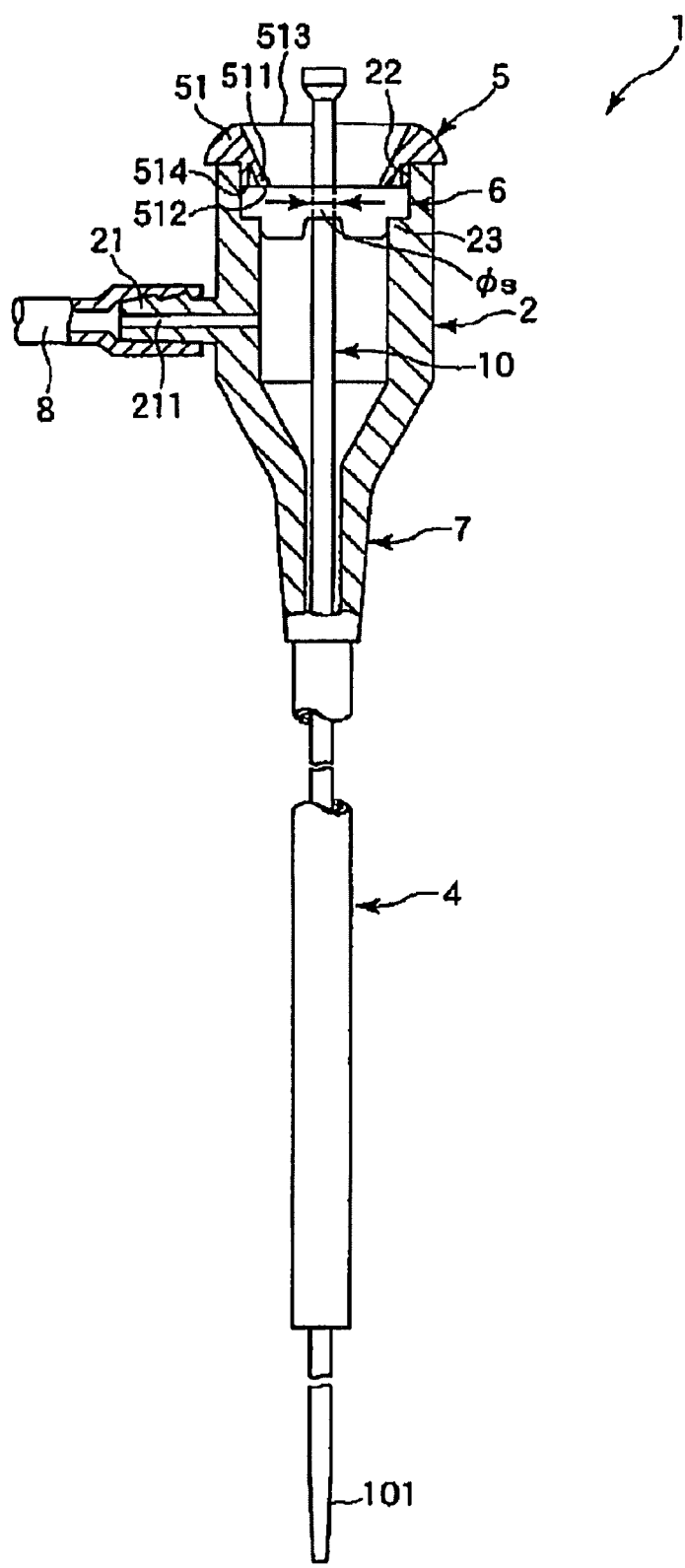
FIG. 1 is a partial vertical cross-sectional view of an embodiment of a medical tool embodying the valve body disclosed here, wherein the medical tool is in the form of an introducer.

The lid member 51 includes a projecting rib 511 on the inner circumferential face portion of the lid member 51. In the illustrated embodiment, the rib is a cylindrical rib 511 on the inner circumferential face portion of the lid member 51 that projects in an oblique distal end direction. In particular, as shown in FIG. 1, the inner diameter and the outer diameter of the rib 511 gradually decrease from the proximal end toward the distal end.

The proximal end portion of the lid member 51 forms an insertion port to allow an elongated member such as the dilator 10, a catheter or a guide wire to be inserted into the sheath 7.

The dilator 10 is in the form of a flexible pipe body (tube). The dilator 10 is inserted into (positioned in) the sheath 7 and is inserted (introduced) into a living organism in a state wherein it is fixed to the sheath 7. Further, to facilitate introduction of the dilator 10, for example, into a blood vessel, the outer diameter of the distal end portion 101 of the dilator 10 narrows or decreases (gradually narrows or decreases) toward the distal end.

The dilator 10 having a configuration as described above is removed from the sheath 7 after the sheath tube 4 is inserted into a living organism (blood vessel). Thereafter, a catheter or a guide wire is inserted through the opening (proximal end opening) 513 at the proximal end of the lid member 51.

As mentioned above, the sealing means 5 includes the valve body 6.

Figure 2:
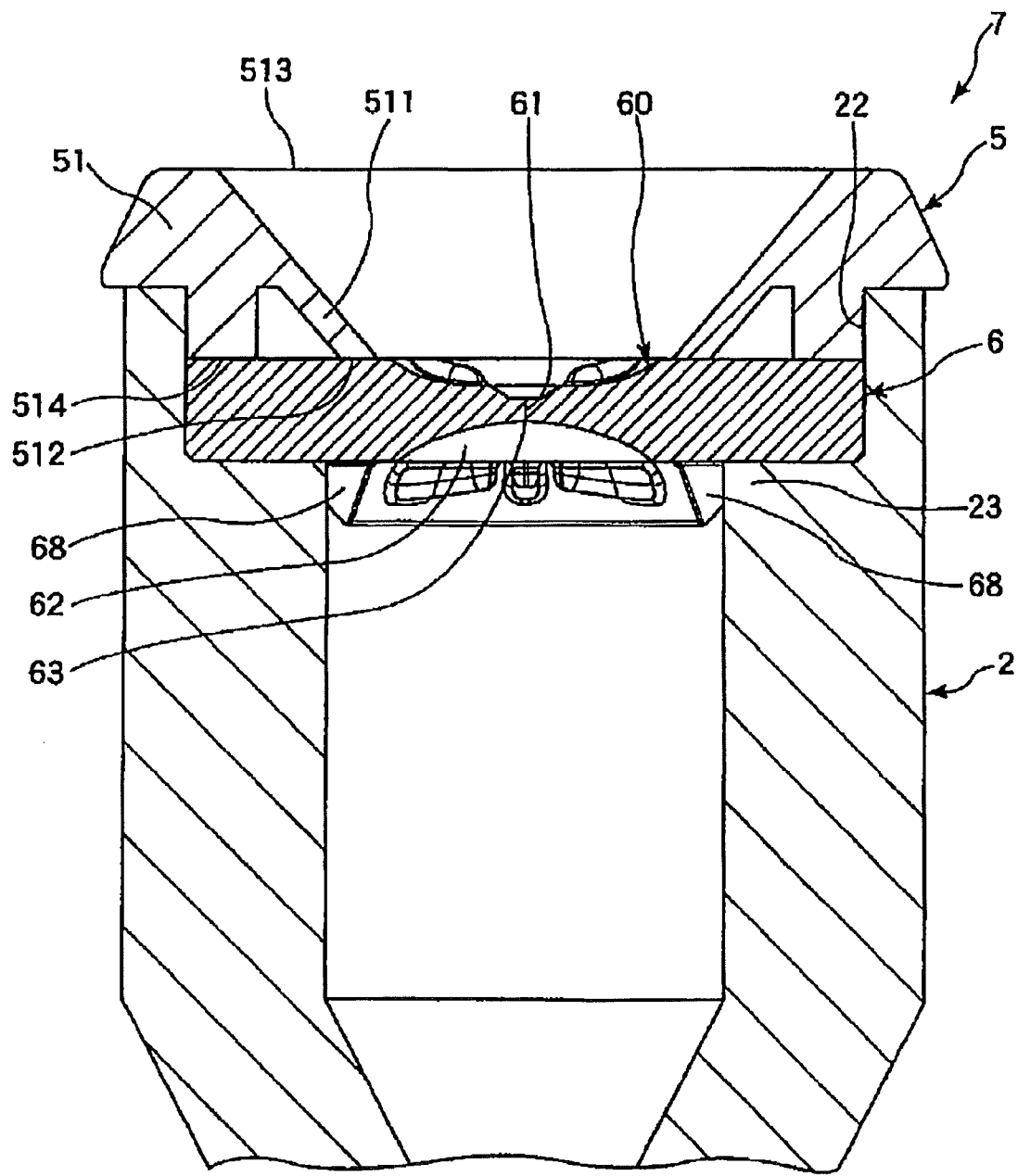
FIG. 2 is a vertical cross-sectional view of the hub, lid member and valve body of the introducer shown in FIG. 1.

As shown in FIGS. 1-4 and 8, the valve body 6 is comprised of a plate-shaped elastic body possessing a pair of end faces. In particular, the elastic body has an upper face (one face) 601 and a lower face (the other face) 602, and is in the shape of an elliptic or circular film (disk form). This valve body 6 is secured in a liquid-tight manner to the hub 2 by virtue of being sandwiched between a stepped portion 23 at the proximal end portion of the hub 2 on the one hand and the distal end face 514 of the lid member 51 and the distal end face 512 of the rib 511 on the other hand as illustrated in FIGS. 1 and 2. In the introducer 1 (sheath 7), the portion surrounded by the distal end face 514 of the lid member 51 and the distal end face 512 of the rib 511 functions as a "mounting section (installation section)" on which the valve body 6 is mounted (installed).

The shape of the valve body 6 in a natural state as viewed in plan, that is the shape of the valve body 6 before it is mounted on the hub 2 as viewed in plan, is an elliptical shape as shown in FIGS. 7 and 14. The shape of the valve body 6 in a mounted state in which it is mounted on the hub 2 (this state is hereinafter referred to simply as the "mounted state") as viewed in plan, has a circular shape as shown in FIG. 12. When the valve body 6 is mounted on the hub 2, the valve body 6 is deformed by virtue of being compressed toward an intersecting portion 63 (hereinafter described) along the major axis direction. Consequently, the valve body 6 takes on a circular shape as viewed in plan. Here, the "natural state" refers to a state in which no external force is applied to the valve body 6.

Although the dimension of the valve body 6 is not specifically restricted, the major diameter of the valve body 6 in the natural state preferably is approximately 5 to 20 mm, more preferably approximately 8 to 12 mm. The major diameter of the valve body 6 in the natural state is preferably greater than the sum total of the inner diameter of the proximal end inner circumferential portion 22 of the hub 2 and the maximum width w1 of a first slit 61. With this relative configuration, sealability (sealing performance) of an opening and closing section 60 of the valve body in the mounted state is obtained.

The minor diameter of the valve body 6 is preferably approximately 4 to 16 mm, more preferably approximately 7 to 10 mm.

The thickness of the valve body 6 is preferably approximately 0.5 to 3 mm, more preferably approximately 0.8 to 1.5 mm.

The material forming the valve body 6 is not restricted to a specific material. Elastic materials such as, for example, natural rubber, various synthetic rubbers such as isoprene rubber, silicone rubber, urethane rubber, styrene-butadiene rubber, fluororubber and acrylic rubber, and various plastic elastomers of polyamide-based elastomer and polyester-based elastomer may be used.

The valve body 6 includes a first concave portion 64 whose bottom face is a curved concave face (curved concave face) 641. The first concave portion 64 is on the upper face side 601 of the valve body 6 (i.e., the side facing away from the interior of the hub 2). In particular, the first concave portion 64 is bowl-shaped. Further, the first concave portion 64 is elliptical or circular in shape as viewed in plan and is disposed such that a central portion (center) of the first concave portion 64 and the central portion (center) of the valve body 6 coincide with each other. The end face of the valve body 6 which is on the side opposite the concave face (bottom face) 641 is the lower face 602. The valve body 6 is disposed relative to the hub 2 such that the concave face 641 (upper face 601) is exposed (positioned) to the outer side of the sheath 7 while the lower face 602 is exposed in the flow path (in the interior of the hub 2) of the sheath 7.

When the dilator (elongated member) 10 is inserted into or positioned in the valve body 6, the distal end portion 101 of the dilator 10 can be introduced to or inserted into a portion of the first slit 61 corresponding to the intersecting portion 63 hereinafter described by the first concave portion 64. Consequently, damage to any portion other than the first slit 61 and a second slit 62 by the dilator 10 can be avoided or prevented. Further, it is possible to inhibit or prevent the distal end portion 101 of the dilator 10 from being crushed or deformed.

The dimension of the first concave portion 64 is not specifically limited. By way of example, the depth (maximum depth) of the central portion (center) of the first concave portion 64 is preferably greater than 0.3 mm, more preferably greater than 0.4 mm, and further preferably is approximately 0.4 to 0.7 mm.

As shown in FIGS. 3-8, 11-14 and 16, the valve body 6 has an opening and closing section 60 which is opened or closed in response to insertion or removal of the dilator 10 (elongated member).

The opening and closing section 60 is composed of a first slit 61, a second slit 62, a second concave portion 65 and two third concave portions 66.

The first slit 61 is formed such that it extends to the concave face 641 (upper face 601) but does not extend to the lower face 602. In other words, the first slit 61 is formed such that it extends only to the concave face 641 (upper face 601) from the inside of the valve body 6 (i.e., the first slit 61 extends through only a portion of the thickness of the valve body or through less than the entirety of the valve body).

This first slit 61 is formed as a straight line which coincides with (or extends in parallel to) the minor axis of the valve body 6 as viewed in plan and is included in the first concave portion 64 as viewed in plan. In other words, the valve body 6 is formed in a straight line from one end portion to the other end portion of the first concave portion 64. Consequently, in the mounted state, the first slit 61 (opening and closing section 60) can be opened and closed readily and with relative certainty.

Figure 5:
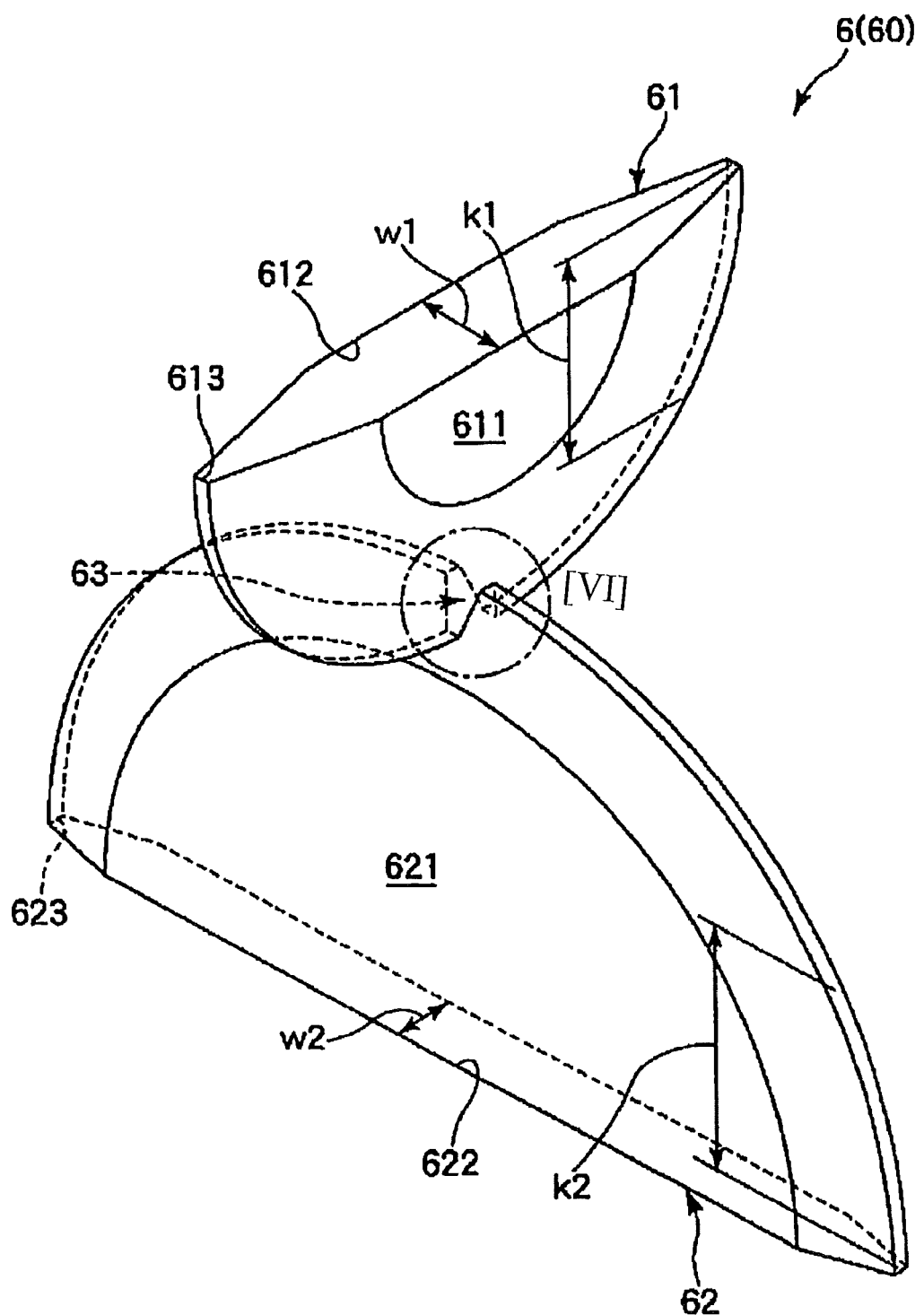
FIG. 5 is a perspective view showing a first space defined by an inner face of a first slit and a second space defined by an inner face of a second slit of the valve body (in the natural state) shown in FIG. 3.

As shown in FIG. 5 (also in FIGS. 3 and 7), the first slit 61 is opened (open) in the natural state. Consequently, in the first slit 61, a first space 611 is formed by (bordered by) inner faces 612 of the first slit. This first space 611 has a semicircular disk shape (flattened shape). The first slit 61 is deformed in such a manner that it is compressed toward the intersecting portion 63 along the major axis direction when the valve body 6 is mounted on the hub 2, and consequently is closed by the mounting. In other words, in the mounted state, the first slit 61 is closed.

Further, the second slit 62 is formed such that it extends to (opens to) the lower face 602 but does not extend to (open to) the concave face 641 (upper face 601). In other words, the second slit 62 is formed such that it extends only to the lower face 602 from the inside of the valve body 6 (i.e., the second slit 62 extends through only a portion of the thickness of the valve body or through less than the entirety of the valve body thickness).

This second slit 62 is formed such that it coincides with (or extends in parallel to) the major axis of the valve body 6 as viewed in plan, that is, the shape of the second slit 62 is a straight line shape as viewed in plan (refer to FIG. 14). Consequently, in the mounted state, the opening and closing section 60 can be opened and closed readily and with certainty. The second slit 62 is elongated in a direction of elongation (i.e., the left-right direction as seen with reference to FIG. 14).

As shown in FIG. 5 (also in FIGS. 4 and 14), the second slit 62 is opened (open) in the natural state in a manner similar to the first slit 61. Consequently, in the second slit 62, a second space 621 is formed by the inner faces 612. This second space 621 is semicircular disk-shaped (flattened shape). In the mounted state, the second slit 62 is partly closed (partly open).

The first slit 61 and the second slit 62 configured in the manner described above and illustrated in the drawing figures partly intersect each other in the inside of the valve body 6 (at an interior portion of the valve body spaced inwardly from the opposite outermost faces of the valve body 6). The first space 611 and the second space 621 communicate with each other, as seen for example in FIG. 5, through the intersecting portion 63 at which the slits intersect each other (the intersecting portion 63 between the first slit 61 and the second slit 62).

When the valve body 6, with the first slit 61 and the second slit 62 communicating with each other in this manner in the natural state, is mounted on the hub 2, the first slit 61 and the second slit 62 are compressed (pressed) in their closing direction by the proximal end inner circumferential portion 22 of the hub 2 (refer to FIG. 11). Therefore, in the first slit 61, the inner faces 612 are pressed against each other and placed into a closely contacting (closed) state. However, by the elastic force of the valve body 6 itself (restoring force by which the first slit 61 tends to be opened), the degree of the close contact is reduced to such a degree that the occurrence of blocking is suppressed (or prevented). Similarly, in the second slit 62, inner faces 622 are pressed against each other and placed into a closely contacting state. However, by the elastic force of the valve body 6 itself (restoring force by which the second slit 62 tends to be opened), the degree of the close contact is reduced to such a degree that occurrence of blocking is suppressed (or prevented).

If radiation sterilization (for example, electron beam sterilization, γ ray sterilization, X-ray sterilization or the like) is carried out, the occurrence of excessive (excessively firm) blocking between the inner faces 612 of the first slit 61 or between the inner faces 622 of the second slit 62 is inhibited or prevented from occurring with relative certainty. Even with silicone rubber with which a sticking phenomenon of the inner faces is known to occur, the occurrence of blocking is inhibited or prevented with relative certainty. Consequently, when an elongated medical member such as the dilator 10 is inserted into the valve body 6 for the first time after the sterilization (hereinafter referred to simply as "upon first time insertion"), the inner faces 612 (also the inner faces 622) exfoliate from each other readily, and consequently, the penetration resistance is reduced and the operation involving insertion and removal of the elongated medical member can be readily carried out. Further, when an elongated medical member is inserted and removed, damage to the first slit 61 or the second slit 62 can be prevented with relatively good certainty.

As shown in FIG. 5, the depth k1 of the first space 611 gradually decreases toward the direction away from the intersecting portion 63. In other words, a portion (bottom face 613) of the first slit 61 which becomes the bottom of the inner faces 612 is curved in an arcuate manner. Consequently, when the dilator 10 is inserted into the first slit 61, the distal end portion 101 of the dilator 10 is guided so as to be directed toward the intersecting portion 63. This facilitates the insertion operation. Further, the distal end portion 101 of the dilator 10 is inhibited or prevented from piercing (penetrating) a portion of the first slit 61 other than the intersecting portion 63 until it comes to the second slit 62, and consequently, damage to the valve body 6 can be inhibited or prevented.

Further, as shown in FIG. 5, the width w1 of the first space 611 gradually decreases toward the bottom face 613 (intersecting portion 63). Consequently, when the dilator 10 is inserted into the first slit 61, the distal end portion 101 of the dilator 10 is guided so as to be directed to the intersecting portion 63, and consequently, the insertion operation can be carried out with relatively good certainty.

The maximum depth k1 of the first slit 61 is not restricted specifically, but is preferably, for example, approximately 35 to 90% of the thickness of the valve body 6, more preferably approximately 40 to 80% of the thickness of the valve body 6.

Although the bottom face 613 of the first slit 61 in the configuration shown in FIG. 5 is a curved face curved in an arcuate manner, the shape of the bottom face 613 is not limited to this. For example, the bottom face 613 may have a V-shape whose apex (vertex) is the intersecting portion 63.

As shown in FIG. 5, the depth k2 of the second space 621 gradually decreases toward the direction away from the intersecting portion 63 similarly to the first space 611. In other words, a portion (bottom face 623) of the second slit 62 which is the bottom of the inner faces 622 is curved in an arcuate manner.

Further, the width w2 (refer to FIG. 5) of the second space 621 gradually decreases toward the bottom face 623 (intersecting portion 63).

The second slit 62 is pressed, in the mounted state, in the direction in which it is closed, that is in the minor axis direction, and is pressed also in its opening direction, that is in the major axis direction. Therefore, as shown in FIG. 11, in the second slit 62 in the mounted state, a portion at which the inner faces 622 closely contact each other (are closed) and another portion at which the inner faces 622 remain spaced away from each other are formed.

Consequently, the contact area of the inner faces 622 of the second slit 62 decreases, and therefore, the area of a portion at which blocking is likely to occur when radiation sterilization is carried out (area over which the inner faces 622 stick to each other) can be decreased. Consequently, since the inner faces 622 of the second slit 62 exfoliate readily from each other, occurrence of damage to the second slit 62 is inhibited or prevented, and the dilator 10 can be readily inserted into the valve body 6.

In this manner, from a relative standpoint, the first slit 61 which is positioned on the insertion side of an elongated medical member exhibits a higher degree of close contact than the second slit 62. Here, the "degree of close contact" signifies the close contact area and the close contacting force between the inner faces.

By adjusting the pressing force (close contacting force) between the inner faces 612 of the first slit 61 in the mounted state, blocking of the portion of the first slit 61 when radiation sterilization is carried out can be suppressed to the minimum while the sealing performance of the opening and closing section 60 is facilitated or assured.

Further, a portion at which the inner faces 622 are closed is formed in the second slit 62 in the mounted state as described above, and the sealability (sealing performance) of the opening and closing section 60 is obtained by cooperation with the first slit 61 closed in the mounted state. In other words, the liquid-tightness of the inside of the hub 2 is achieved or assured, and leakage of liquid (for example, blood) filled in the hub 2 can be inhibited or prevented with relatively good certainty.

It is to be understood that the second slit 62 may be entirely closed in the mounted state in a manner similar to the first slit 61.

Further, the maximum depth k2 of the second slit 62 is not specifically restricted and preferably is, for example, approximately 35 to 90% of the thickness of the valve body 6, more preferably approximately 40 to 80% of the thickness of the valve body 6.

The bottom face 623 of the second slit 62 in the configuration shown in FIG. 5 is formed as a curved face that is curved in an arcuate manner, the shape of the bottom face 623 is not limited to this. For example, the bottom face 623 may have a V-shape whose apex (vertex) is the intersecting portion 63.

As shown in FIG. 5, the first slit 61 and the second slit 62 intersect crosswise with each other at the portion at which the depth of them is in the maximum such that the intersecting angle is 90°. Naturally, the intersecting angle of these slits 61 and 62 is not limited to 90°.

The intersecting portion 63 between the first slit 61 (first space 611) and the second slit 62 (second space 621) is shared by both of the first slit 61 and the second slit 62 and is set to a middle portion (central portion) of the valve body 6 as viewed in plan. In other words, the intersecting portion 63 is positioned at a central portion of the first concave portion 64 as viewed in plan and is included within the first concave portion 64. Consequently, when the dilator 10 is inserted into and removed from the valve body 6 (opening and closing section 60), the operation can be carried out relatively stably.

Referring to FIG. 8, the length L of the intersecting portion 63 is not specifically restricted. By way of example, the length L is preferably approximately 10 to 50% of the thickness of the valve body 6, more preferably approximately 15 to 35% of the thickness of the valve body 6. The intersecting portion 63 is described in more detail below.

Figure 6:
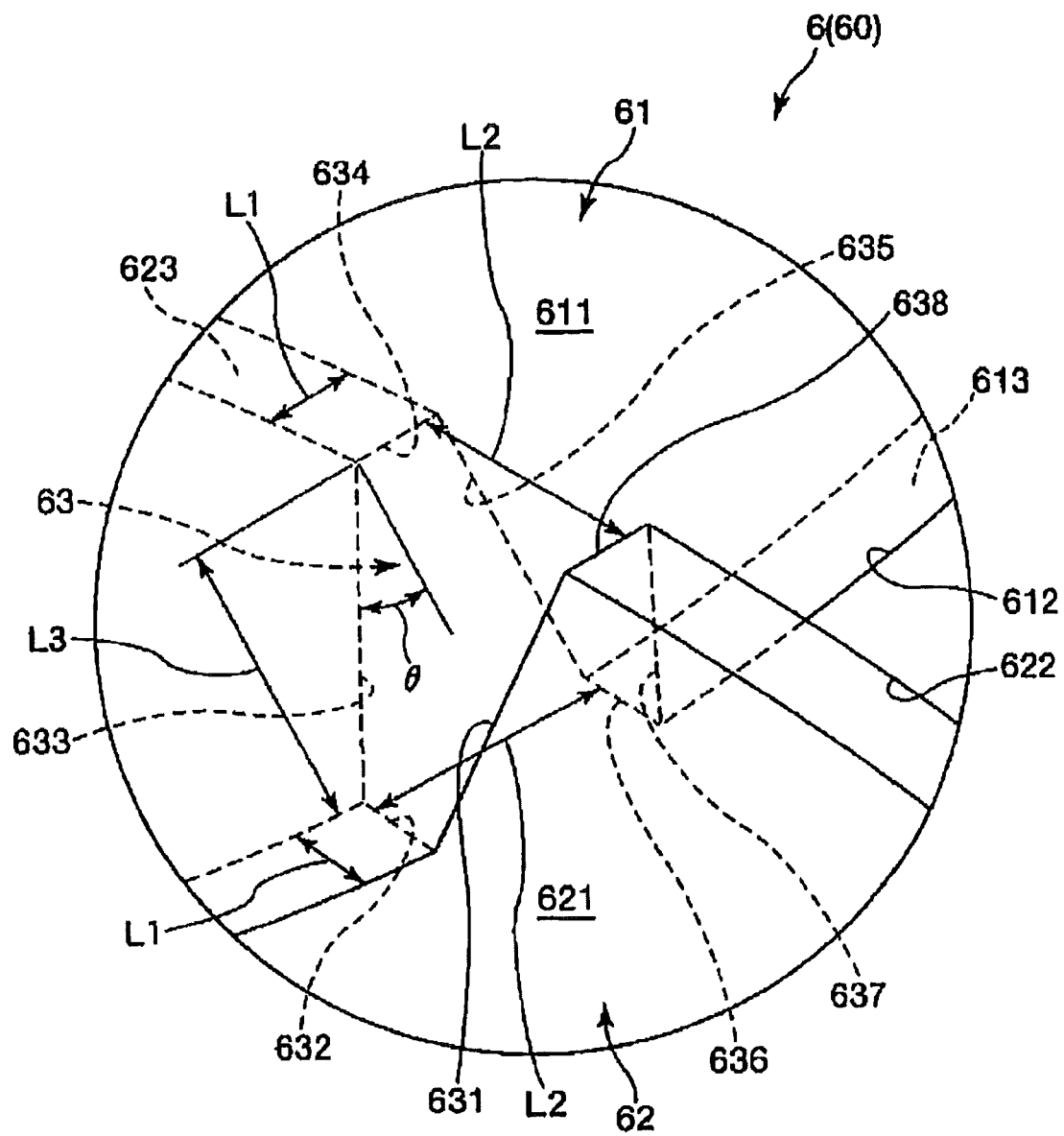
FIG. 6 is an enlarged detailed view of the region [VI] surrounded by an alternating long and short dash line in FIG. 5.

As shown in FIG. 6 and also in FIG. 5, the intersecting portion 63 is a space having the shape of a hexahedron in the natural state of the valve body. This intersecting portion 63 (hexahedron) has 12 sides which form the same, and the sides include eight sides which are given as nodal lines formed by intersection of the inner faces 612 of the first slit 61 and the inner faces 622 of the second slit 62 (in FIG. 6, the sides 631, 632, 633, 634, 635, 636, 637 and 638).

Though the sum total of the lengths of the sides 631-638 is not restricted, it is preferably 1.0 to 6.0 mm, more preferably 1.5 to 4.5 mm. If the sum total is within this numerical value range, an elongated medical member which is normally used (inserted) in the introducer 1 can be inserted into and pulled out from the valve body 6 in an appropriate manner (smoothly without damaging the first slit 61 and the second slit 62) without relying upon the outer diameter $\phi s$ (shown in FIG. 1) of a portion of the elongated member to be inserted into a living organism. Further, in a state in which the elongated medical member is fitted in the valve body 6, the sealing performance of the opening and closing section 60 is also properly maintained.

Although the length L1 of the sides 632, 634, 636, 638 which extend parallel to the upper face 601 and the lower face 602 of the valve body 6 is not specifically limited, the length L1 is preferably 0.1 to 0.5 mm. If the length L1 is within this numerical value range, no edge exists at the intersecting portion 63. Accordingly, even if the distal end portion 101 of the dilator 10 strikes the bottom face 613, it is reliably inhibited or prevented from making a starting point of damage to the first slit 61 and the second slit 62.

The length L2 of the four sides other than the nodal lines (distance between the side 634 and the side 638 and distance between the side 632 and the side 636) is not restricted specifically, but is preferably 0.1 to 0.7 mm.

The length L3 of the intersecting portion 63 which extends perpendicularly to the upper face 601 and the lower face 602 of the valve body 6 is not limited to a specific value, but is preferably 0.2 to 0.6 mm.

Similarly, the angle $\theta$ defined by the direction of the length L3 (a line parallel to the length L3) and the sides 631, 633, 635 and 637 which do not extend parallel to the upper face 601 and the lower face 602 of the valve body 6 is not specifically limited. However, the angle $\theta$ is preferably 5 to 40°. When the angle $\theta$ is within this numerical value range, when the valve body 6 is mounted on the hub 2, the occurrence of excessive blocking between the inner faces 612 of the first slit 61 or between the inner faces 622 of the second slit 62 is inhibited or prevented with relatively good certainty. Further, the penetration resistance is reduced and an operation when an elongated medical member is inserted and pulled out can be carried out quite readily.

The outer diameter $\phi s$ of the elongated medical member permitted to be fitted into the opening and closing section 60 of the valve body 6 is not limited to a specific size. By way of example, the maximum value of the outer diameter $\phi s$ of the elongated medical member is 6 to 7 mm, more preferably 6.5 to 7 mm. Meanwhile, the minimum value is preferably 0.1 to 0.3 mm, more preferably 0.1 to 0.2 mm.

The manner of forming or fabricating the first slit 61 and the second slit 62 is not limited. By way of example, the valve body 6 is preferably molded by compression molding, LIM molding, transfer molding or the like, and during this formation the first slit 61 and the second slit 62 are preferably formed simultaneously.

As described above, the opening and closing section 60 (valve body 6) has the second concave portion 65 and the third concave portions 66. The second concave portion 65 and the third concave portions 66 are formed on the concave face 641 (upper face 601) side.

Figure 9:
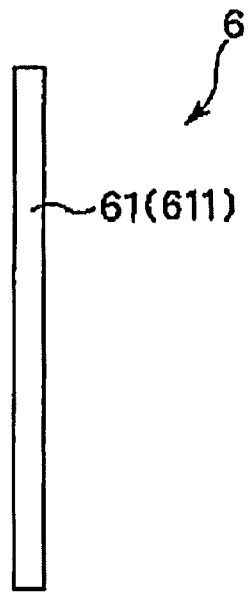
FIG. 9(a) is plan view of the first slit of the valve body (in the natural state) shown in FIG. 3.
FIG. 9(b) is a plan view of a second concave portion and a third concave portion of the valve body (in the natural state) shown in FIG. 3.
Figure 9:
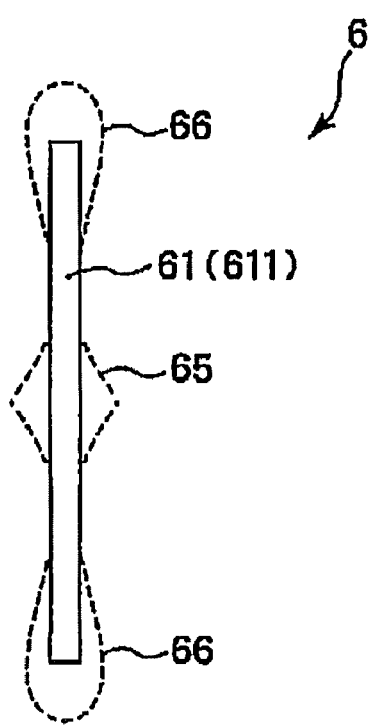

Here, in order to facilitate recognition of the second concave portion 65 and the third concave portions 66 (in order that the first slit 61 and the second concave portion 65 and third concave portions 66 can be distinguished readily from each other), only the first slit 61 of the valve body 6 is shown in FIG. 9(a), and the first slit 61, the second concave portion 65 and the third concave portions 66 of the valve body 6 are shown in FIG. 9(b). Further, in FIGS. 9(a) and 9(b), the first slit 61 is indicated by a solid line and the second concave portion 65 and the third concave portions 66 are indicated by dotted lines (broken lines).

From a similar reason, the valve body 6 on which the second concave portion 65 and the third concave portions 66 are not formed is shown in FIG. 10(a), and the valve body 6 on which the second concave portion 65 and the third concave portions 66 are formed is shown in FIG. 10(b). Further, in FIG. 10(b) slanting lines, which do not exist on a proper cross-sectional view of the valve body, are applied only to the second concave portion 65 and the third concave portions 66.

As shown in FIGS. 3 and 7-10, the second concave portion 65 is formed at a middle portion of the valve body 6 on the concave face 641 (upper face 601) side, that is, a location (position) of the first concave portion 64 corresponding to the intersecting portion 63. The second concave portion 65 is formed, in the thicknesswise direction of the valve body 6 (in the upward and downward direction), to an intermediate portion of the first slit 61 but does not extend to the second slit 62. Further, at the opposite end portions of the first slit 61 of the valve body 6 on the concave face 641 side, the third concave portions 66 are formed.

The second concave portion 65, third concave portions 66 and first slit 61 are communicated with each other in the natural, state and generally form a single groove (concavity).

Further, while, in the natural state, the second concave portion 65 exhibits a diamond shape (quadrangle) such as shown in FIGS. 3 and 7. The shape of the second concave portion 65 need not be a quadrangular shape, as it can also be a circular shape. As shown in FIG. 8, a bottom face 651 in the second concave portion 65 is a flat face substantially perpendicular to the moving direction (longitudinal direction of the dilator 10) upon insertion and pulling out of the dilator 10, and side faces 652 are inclined by a predetermined angle with respect to the moving direction upon insertion and pulling out of the dilator 10. The inclination angle $\theta 1$ of the side faces 652 with respect to the moving direction preferably is 45° or more in the natural state, more preferably 60°, and further more preferably approximately 60 to 80°.

Although the dimension of the second concave portion 65 is not restricted, it is preferably set to such a value that, when the dilator 10 is inserted into the valve body 6, the distal end portion 101 of the dilator 10 does not catch the second concave portion 65, and for example, the length a (refer to FIG. 8) of the first slit 61 of the bottom face 651 preferably is set to a value smaller than the outer diameter of the distal end portion 101 of the dilator 10. Specifically, the length a of the first slit 61 of the bottom face 651 preferably is approximately 0.2 to 0.4 mm in the natural state. Further, the depth b of the second concave portion 65 in the natural state preferably is 0.1 mm or more, more preferably approximately 0.1 to 0.2 mm.

As shown in FIG. 12, when the second concave portion 65 is mounted on the hub 2, it is deformed so as to be compressed toward the intersecting portion 63 along the major axis direction, and consequently, it is deformed such that the width thereof decreases. However, in the mounted state, the second concave portion 65 does not fully closely contact the intersecting portion 63.

By virtue of this second concave portion 65, the contact area of the inner faces 612 of the first slit 61 is decreased, and consequently when radiation sterilization is carried out, the area over which blocking occurs can be reduced. Further, upon insertion for the first time, the second concave portion 65 makes a start of exfoliating at the first slit 61 which may be in a sticking state. Consequently, upon insertion for the first time, exfoliating at the first slit 61 occurs rather readily, and otherwise possible damage to the first slit 61 or the second slit 62 can be inhibited or prevented. Further, the penetration resistance upon insertion for the first time decreases, and the dilator 10 can be quite readily inserted into the valve body 6.

In the natural state, the pair of third concave portions 66 have a rather rounded shape as viewed in plan. As shown in, for example, FIGS. 3 and 12, each of the third concave portions 66 extends over (i.e., spans) the inside and the outside of the first concave portion 64 (extends from the inside of the first concave portion 64 to the outside of the first concave portion 64).

As shown in FIG. 12, each of the third concave portions 66 is deformed such that, when the valve body 6 is mounted on the hub 2, the third concave portion 66 is compressed toward the intersecting portion 63 along the major axis direction, and consequently, it is deformed such that the width thereof decreases. However, in the mounted state, the third concave portion 66 does not fully closely contact the intersecting portion 63.

By those third concave portions 66, the contact area of the inner faces 612 of the first slit 61 is decreased, and consequently, the area over which blocking occurs when radiation sterilization is carried out can be decreased. Consequently, upon insertion for the first time, the first slit 61 exfoliates quite readily, and the occurrence of damage to the first slit 61 or the second slit 62 can be inhibited or prevented. Further, the penetration resistance upon insertion for the first time decreases, and the dilator 10 can be inserted into the valve body 6 rather readily.

By virtue of the third concave portions 66, the volume of the opposite end portions of the first slit 61 (first space 611) of the valve body 6 decreases, the resistance (sliding resistance) when the dilator 10 is inserted into the valve body 6 or pulled out from the valve body 6 decreases. Consequently, the sliding performance of the dilator 10 is enhanced, and it is possible to readily insert the dilator 10 into the valve body 6 or pull out the dilator 10 from the valve body 6.

Since the third concave portions 66 are provided at the opposite end portions of the first slit 61, even if the third concave portions 66 are made comparatively large, this does not have any influence on the sealing performance of the opening and closing section 60.

Further, as shown in FIG. 8, the total value of the areas of the third concave portions 66 on a vertical section taken along the first slit 61 (as viewed in side elevation parallel to the first slit 61) in the natural state preferably is greater than the area of the second concave portion 65. More preferably, the area of each of the third concave portions 66 is greater than the area of the second concave portion 65.

Consequently, the sliding performance of the dilator 10 is further improved, and it is possible to insert the dilator 10 into the valve body 6 or pull out the dilator 10 from the valve body 6 more readily.

In the illustrations, the shapes and the dimensions of the pair of third concave portions 66 are the same as each other. However, they may be different from one another.

The dimensions of the third concave portions 66 are not specifically restricted, but the depths of the third concave portions 66 in the illustrated configuration are equal to the depth of the first slit 61.

A plurality of projections 67 (second projections) are provided on the concave face 641 side of the valve body 6. In the illustrated embodiment, four projections 67 are provided. The projections 67 are positioned in the first concave portion 64 and are disposed such that they are opposed to each other through the first slit 61.

In the configuration shown, the four projections 67 are disposed such that they are line-symmetrical with respect to the first slit 61 and are point-symmetrical with respect to the intersecting portion 63 (center of the valve body 6) as viewed in plan. Further, the projections 67 are positioned to extend radially from the intersecting portion 63 as viewed in plan.

In the configuration shown, the shapes and the dimensions of the projections 67 are the same as each other, but they may be different from each other. The projections 67 are preferably elongated in shape, meaning that their radial extent (i.e., dimension in the radial direction relative to the center of the first concave portion 64) is greater than their width-wise extent (width dimension).

The dimensions of the projections 67 are not specifically limited to certain values. However, as an example, the height of the projections 67 is preferably approximately 0.1 to 0.5 mm, more preferably approximately 0.2 to 0.3 mm.

The illustrated configuration shows two pairs of projections 67, but the number of projections 67 is not restricted to this. For example, only one pair of projections 67 may be provided or three or more pairs of projections 67 may be provided. Also, the number of projections 67 may be an odd number disposed in a non-symmetrical arrangement with respect to the first slit 61.

As shown in FIG. 13, when the dilator 10 is moved downwardly and inserted into the valve body 6, the valve body 6 curves such that a central portion of the valve body is displaced downwardly and the projections 67 contact (point-contact) the outer circumferential face of the dilator 10. Consequently, the contact area between the outer circumferential face of the dilator 10 and the valve body 6 decreases, and the resistance (sliding resistance) when the dilator 10 is inserted into the valve body 6 decreases. Consequently, the sliding performance of the dilator 10 is improved, and the dilator 10 can be inserted into the valve body 6 rather readily.

Further, when the dilator 10 is inserted into the valve body 6, the dilator 10 is guided by the projections 67 such that it is directed to a central portion of the valve body 6, that is toward the intersecting portion 63. Consequently, the dilator 10 can be readily inserted into the valve body 6, and damage to the valve body 6 can be inhibited or prevented.

As shown in FIGS. 4, 8 and 14-16, ribs (wall portions) 68 and projections (first projections) 69 are formed on the lower face 602 side of the valve body 6. The sliding performance of the dilator 10 is improved by the ribs 68 and the projections 69, and insertion and pulling out of the dilator 10 can be carried out rather readily and the sealability (sealing performance) of the opening and closing section 60 is improved. The ribs 68 and the projections 69 are described below in more detail.

A pair of ribs 68 extending along the lower face 602 are formed on the lower face 602 side of the valve body 6. The ribs 68 have an arcuate shape. Further, the ribs 68 are disposed in an opposing relationship to each other with the second slit 62 interposed therebetween. The ribs 68 are positioned so that adjacent ends of the two ribs are spaced from one another, with an imaginary continuation of the line of extension of the second slit 62 passing between the adjacent ends of the two ribs 68. In the mounted state, the outer peripheral surfaces (outer sides) of the ribs 68 contact the inner circumferential surface of the hub 2.

In the configuration shown in FIG. 14, the ribs 68 are disposed such that they are line-symmetrical with each other with respect to the second slit 62 and point-symmetrical with each other with respect to the intersecting portion 63 as viewed in plan.

As shown in FIG. 2, when the valve body 6 is mounted on the hub 2, the outer peripheral faces (outwardly facing arcuate surfaces) of the ribs 68 contact the inner circumferential surface of the hub 2. Consequently, when the valve body 6 is deformed such that it is compressed toward the intersecting portion 63 along the major axis direction, the second slit 62 is inhibited or prevented from being opened further. Consequently, the sealing performance of the opening and closing section 60 is maintained.

Further, when the inside of the hub 2 is placed into a negative pressure state, although the valve body 6 is pulled (downwardly) into the hub 2, since the outer peripheral surface of the ribs 68 contacts the inner circumferential face of the hub 2 and the valve body 6 is reinforced by the ribs 68, deformation of the valve body 6 is restrained and the second slit 62 inhibited or prevented from being opened further. Consequently, the sealing performance of the opening and closing section 60 is maintained.

Although the dimensions of the ribs 68 are not specifically restricted, by way of example, the height c (shown in FIG. 15) of the ribs 68 is preferably 0.3 mm or more, more preferably approximately 0.3 to 1.3 mm, and further preferably approximately 0.5 to 1 mm.

Further, referring to FIG. 14, the length d of the ribs 68 in the direction of the second slit 62 preferably is greater than the length of the second slit 62, and preferably is equal to, for example, approximately 3 to 7 times the length of the second slit 62, more preferably approximately 3.5 to 6 times the length of the second slit 62. In the configuration shown, the length d of the ribs 68 is greater than the length of the second slit 62.

A predetermined gap is provided between end portions 681 of one of the ribs 68 and end portions 681 of the other one of the ribs 68. In other words, the ribs 68 are not present on an extension line of the second slit 62 as viewed in plan (i.e., an extension line of the second slit 62 does not cross or intersect either of the ribs 68).

Consequently, where the valve body 6 is deformed such that it is compressed toward the intersecting portion 63 along the major axis direction when it is mounted on the hub 2, a relief corresponding to the deformed portion is generally assured. Consequently, the valve body uniformly contacts (closely contacts) the hub 2, and the liquid-tightness of the inside of the hub 2 is maintained with relative certainty.

Further, the resistance (sliding resistance) when the dilator 10 is moved (inserted and pulled out) with respect to the valve body 6 can be inhibited or prevented from increasing unnecessarily. Consequently, the sliding performance of the dilator 10 is improved, and insertion and pulling out of the dilator 10 can be carried out relatively readily.

Referring to FIG. 14, the gap distance f between the end portion 681 of one of the arcuate-shaped ribs 68 and the adjacent end portion 681 of the other arcuate rib 68 is preferably such that, in the mounted state, an end portion of one of the ribs 68 and the adjacent end portion of the other rib 68 do not contact each other. In particular, in the natural state, the gap distance f preferably is approximately 0.5 to 3 mm, more preferably approximately 1 to 2 mm.

As further shown in FIG. 14, in the natural state, the distance e between the outer peripheral surface of one of the ribs 68 and the outer peripheral surface of the other rib 68 (twice the radius of curvature of the outer peripheral surface of the ribs 68) is set a little greater than the inner diameter of the hub 2 at a position at which the hub 2 corresponds to or engages/contacts the ribs 68. Consequently, in the mounted state, the portions of the ribs 68 marking the distance e are compressed toward the intersecting portion 63 (in a direction in which the second slit 62 is closed) by the inner circumferential surface of the hub 2. Consequently, the second slit 62 is closed with good reliability.

The shape of the ribs 68 is not limited to the arcuate shape as they may possess a curved shape in which portions have different curvatures such as an elliptic arc, a straight shape (bar shape) or the like.

In the configuration shown, a pair of ribs 68 is provided. However, the number of ribs 68 is not limited to this, but may be two pairs or more, or may be an odd number of ribs non-symmetrically disposed with respect to the second slit 62.

As shown in FIGS. 4 and 14, a plurality of (in the configuration shown, six) projections 69 exist on the lower face 602 side of the valve body 6. The projections 69 are disposed between the pair of ribs 68 and the second slit 62. In other words, the projections 69 are positioned on the inner side of the ribs 68 (between the pair of ribs 68) and are disposed in an opposing relationship to each other with the second slit 62 interposed therebetween.

In the configuration shown in FIG. 14, the six projections 69 are disposed line-sequentially with respect to the second slit 62 and point-symmetrically with respect to the intersecting portion 63 (center of the valve body 6). Further, the projections 69 are positioned radially with respect to the center of the intersecting portion 63 as seen in plan and extend from the ribs 68 toward the intersecting portion 63. The six projections 69 are preferably elongated in shape, meaning that their radial extent (i.e., dimension in the radial direction relative to the center of the lower face 602) is greater than their width-wise extent (width dimension).

The projections 69 on each side of the slit 62 are positioned at equal angular intervals of 45°. In particular, one pair of projections 69 is positioned along the first slit 61 as viewed in plan (i.e., the middle projection on each side of the slit 62 is positioned along the first slit 61), and the other two projections 69 on each side of the slit 62 are positioned at equal angular intervals of 45° on opposite sides of the pair of the projections 69.

As shown in FIG. 16, when the dilator 10 is moved upwardly and pulled out from the valve body 6, the valve body 6 is deformed such that a central portion of the valve body is displaced upwardly and the projections 69 contact (point-contact) with the outer peripheral surface of the dilator 10. Consequently, the contact area of the outer peripheral surface of the dilator 10 and the valve body 6 decreases, and the resistance (sliding resistance) when the dilator 10 is pulled out from the valve body 6 decreases. Consequently, the sliding performance of the dilator 10 is improved, and the dilator 10 can be removed from the valve body 6 rather readily.

Particularly when the dilator 10 is inserted in the valve body 6, the valve body 6 is reinforced by the projections 69, and consequently, the second slit 62 become less likely to be opened. The sealing performance of the opening and closing section 60 is improved by this.

Although the shapes and the dimensions of the projections 69 are not limited, in the configuration shown, distal end portions 691 (end portions on the second slit 62 (intersecting portion 63) side) of the projections 69 are rather rounded, and the projections 69 have the same shape and have the same dimension. The description below describes one projection 69 as representative of all the projections.

The height g of the distal end portion 691 of the projection 69 is preferably greater than 0.2 mm, and is more preferably approximately 0.3 to 0.5 mm.

If the height g is set significantly greater than the lower limit value mentioned above, when an elongated medical member (dilator 10) having a comparatively great outer diameter is to be pulled out and when an elongated member having a comparatively small outer diameter is to be pulled out, the projections 69 are liable to contact the outer peripheral surface of the dilator 10.

On the other hand, where the height g is set lower than the upper limit value given above, the increasing amount of the volume of the valve body 6 can be restricted to a comparatively low value. Consequently, the resistance (sliding resistance) when the dilator 10 is moved (inserted and pulled out) with respect to the valve body 6 can be made comparatively low.

Further, the height of a proximal end portion 692 of the projection 69 (end portion on the rib 68 side) is lower than the height c of the rib 68. Consequently, the increasing amount of the volume of the valve body 6 can be set to a comparatively low value, and the resistance (sliding resistance) when the dilator 10 is moved (inserted and pulled out) with respect to the valve body 6 can be made comparatively low.

Further, in the illustrated configuration shown in FIG. 15, the height g0 of the projection 69 gradually decreases from the outer circumferential portion toward the central portion of the valve body 6, that is from the rib 68 side toward the second slit 62 (intersecting portion 63) side. Consequently, when the dilator 10 is inserted into the valve body 6, the sliding resistance of the valve body 6 can be made comparatively low. It is to be understood that the height g0 of the projection 69 may also be fixed.

The inclination angle θ2 of a lower face 693 of the projection 69 with respect to the lower face 602 is preferably approximately 0 to 10°, more preferably approximately 0 to 8°.

Referring to FIG. 14, the width w0 of the projection 69 gradually decreases from the rib 68 side toward the second slit 62 side. Consequently, when the dilator 10 is inserted into the valve body 6, an increase in the sliding resistance of the valve body 6 can be suppressed.

Further, the projections 69 do not extend all the way to the second slit 62 (i.e., the projections 69 stop short of the slit 62). Consequently, when the dilator 10 is inserted into the valve body 6, the valve body 6 is liable to be deformed such that a central portion of the valve body is displaced downwardly to a suitable degree, and the projections 67 of the upper face 601 side and the outer peripheral face of the dilator 10 can contact each other with relative certainty.

With reference to FIG. 14, all of the gap distances h between the distal end portions 691 of the projections 69 and the lower face 693 are equal to each other. Consequently, when the dilator 10 is pulled out from the valve body 6, the projections 69 and the outer peripheral surface of the dilator 10 can contact each other relatively uniformly. As a result, the dilator 10 can be readily and stably removed from the valve body 6.

Although the gap distance h mentioned above is not specifically limited, in the natural state, it is preferably approximately 0 to 1.5 mm, more particularly approximately 0.3 to 0.5 mm.

There are no projections positioned on an extension line of the second slit 62 as viewed in plan. Consequently, the resistance (sliding resistance) when the dilator 10 is moved (inserted and pulled out) with respect to the valve body 6 can be inhibited or prevented from increasing unnecessarily. As a result, the sliding property of the dilator 10 is improved, and insertion and pulling out of the dilator 10 can be carried out readily.

Further, the projections 69 and the ribs 68 are connected to each other. Consequently, deformation of the valve body 6 is suppressed, and the sealability of the opening and closing section 60 is improved. It is to be understood that the projections 69 may otherwise be spaced from the ribs 68.

In the configuration shown, three pairs of projections 69 are provided, but the number of projections 69 is not limited to this. One pair, two pairs or four or more pairs may be provided, or the number of projections 69 may be an odd number positioned in a non-symmetrical arrangement with respect to the second slit 62. As an example of another preferred configuration of the illustrated arrangement, the two projections 69 at the central location can be eliminated while the other four projections 69 at the opposite end portions remain. In another example of preferred configuration of the illustrated arrangement, the four projections 69 at the opposite end portions can be eliminated so that only the two projections 69 at the central location remain.

Although the valve body 6 is preferably formed as a single member from the same material, the configuration of the valve body 6 is not limited to this. For example, two or more different materials may be used to produce the valve body 6 or a plurality of members may be integrated by fusion, adhesion or the like to produce the valve body 6.

As described above, with the present introducer 1 (valve body 6), the sliding performance of the dilator 10 is improved, and insertion and pulling out of the dilator 10 can be carried out rather readily. Further, the sealability (sealing performance) of the opening and closing section 60 is improved.

Further, even if insertion and pulling out of the dilator 10 is repeated frequently, occurrence of damage to the first slit 61 or the second slit 62 is inhibited or prevented (durability is rather high), and the sealability (sealing performance) of the opening and closing section 60 is maintained. In other words, the liquid-tightness of the inside of the hub 2 is maintained, and leakage of liquid (for example, blood) filled in the hub 2 can be inhibited or prevented with good reliability.

The elongated medical member to be inserted into the sheath 7 through the valve body 6 is not restricted to the dilator 10. Instead, the elongated medical member may be, for example, a catheter or a guide wire.

While the valve body and the medical tool of the present invention are described above in connection with the embodiment shown in the drawings, the present invention is not limited to this. Components can be replaced by alternatives which exhibit similar functions. Further, arbitrary components may be added.

The first slit and the second slit are not limited to those which are open in the natural state, but may be, for example, those which are closed in the natural state.

The first slit and the second slit are not limited to those which have a shape of a straight line as viewed in plan, but only one of the first slit and the second slit may have a shape of a straight line, or the first slit and the second slit may have shapes other than a shape of a straight line.

The medical tool is not limited to an introducer.

While both the first space and the second space are formed such that the depth of each gradually decreases toward the direction away from the intersecting portion, the configuration of the first space and the second space is not limited to this. Indeed, only one space may be formed such that the depth gradually decreases toward the direction away from the intersecting portion.

Although the depth described above gradually decreases toward the direction away from the intersecting portion, the depth is not limited to this, but it may be, for example, uniform.

Both of the first space and the second space have a portion whose width gradually decreases toward the intersecting portion. However, the configuration of the first space and the second space is not limited to this. It is possible for only one of the spaces to have a portion whose width gradually decreases toward the intersecting portion.

WORKING EXAMPLES

Now, particular working examples of the valve body in accordance with the disclosure here are described.

1. Production of the Sheath (Introducer)

Working Example 1

The valve body shown in FIGS. 3-12 was produced by transfer molding using silicone rubber without forming the first concave portion 64, second concave portion 65, third concave portions 66 and projections 67 on the upper face 601 side. Then, the valve body was mounted on the hub to produce the sheath (introducer) shown in FIGS. 1 and 2. Further, to the first slit and the second slit of the valve body, silicone oil (viscosity: 1,000 cSt) was applied. Further, electron beam sterilization (dose: 55 kGy) was carried out on the sheath.

The dimensions of individual portions of the valve body in the natural state are set forth below:
Major axis of the valve body: 8.6 mm
Minor axis of the valve body: 7.7 mm
Thickness of the valve body: 1.3 mm
Height c of the ribs 68: 0.8 mm
Length d of the ribs 68: 5.3 mm
Length e between the outer peripheral faces of the ribs 68: 5.4 mm
Gap distance f between the end portions 681 of the ribs 68: 1.5 mm
Height g of the distal end portions 691 of the projections 69: 0.3 mm
Gap distance h between the distal end portions 691 of the projections 69 and the intersecting portion 69: 0.9 mm
Inclination angle θ2 of the lower face 693 of the projections 69: 8°

Working Example 2

The Working Example 2 was similar to the Working Example 1 except that two projections 69 at the central portion were not formed so that the total number of projections 69 was changed to four.

Working Example 3

The Working Example 3 was similar to the Working Example 1 except that four projections 69 at the opposite end portions were not formed so that the total number of projections 69 was changed to two.

Working Example 4

Working Example 4 was similar to Working Example 1 except that the valve body had a circular shape having a diameter of 8 mm as viewed in plan, and the first slit and the second slit which were closed in the natural state were formed by cutter working, meaning the slits were formed by cutting the material forming the valve body.

Working Example 5

Working Example 5 was similar to Working Example 1 except that the projections 69 were spaced away from the ribs 68.

Comparative Example 1

Comparative Example 1 was similar to Working Example 1 except that the projections 69 were not formed.

Comparative Example 2

Comparative Example 2 was similar to Working Example 1 except that the ribs 68 were not formed.

Comparative Example 3

Comparative Example 3 was similar to Working Example 1 except that the ribs 68 and the projections 69 were not formed.

Comparative Example 4

Comparative Example 4 was similar to Working Example 4 except that the ribs 68 and the projections 69 were not formed.

2. Evaluation

The following evaluation was conducted for the working examples and the comparative examples.
[2.1] Evaluation of the Sealability
A dilator (produced by Terumo Corporation) having an outer diameter of 2 mm was inserted into the valve body of the sheath after the electron beam sterilization, and in this state, the sealability was confirmed in the following manner. Further, the sealability was confirmed in the following manner in a state in which three guide wires having different dimensions were inserted and another state in which nothing was inserted. The three guide wires had outer diameters of 0.89 mm, 0.46 mm and 0.36 mm.

As an evaluation, the opening at the distal end portion of the sheath was sealed, and air was injected into the sheath by 0.3 kgf/cm2 through the side port and a flow of the air was confirmed in water by visual observation.

For: each of the working examples and the comparative examples, the evaluation was carried out with regard to 30 samples with the following criteria.

For each of the working examples and the comparative examples, the evaluation was carried out with regard to 30 samples with the following criteria.

○: excellent

Δ: good x: rather bad

The evaluation above mentioned is shown in Table 1.

TABLE 1

| | | Valve body lower face specification | | | Evaluation | | |
|---|---|---|---|---|---|---|---|
| | | | | | Sliding performance | | Negative pressure |
| | Slits | Ribs | Projections | Sealability | Insertion resistance [gf] | Pulling off resistance [gf] | resisting performance |
| Working example 1 | Transfer molding | Yes | Yes (six) | ○ | 150 | 175 | Δ |
| Working example 2 | Transfer molding | Yes | Yes (four) | ○ | 145 | 180 | Δ |
| Working example 3 | Transfer molding | Yes | Yes (two) | Δ | 140 | 185 | Δ |
| Working example 4 | Cutter working | Yes | Yes (six) | ○ | 150 | 175 | Δ |
| Working example 5 | Transfer molding | Yes | Yes (six) | Δ | 145 | 175 | Δ |
| Com. example 1 | Transfer molding | Yes | No | x | 135 | 200 | x |
| Com. example 2 | Transfer molding | No | Yes (six) | x | 150 | 175 | x |
| Com. example 3 | Transfer molding | No | No | x | 135 | 200 | x |
| Com. example 4 | Cutter working | No | No | x | 135 | 200 | x |

○: excellent

Δ: good x: rather bad

[2.2] Sliding Performance (Sliding Resistance)

A dilator (produced by Terumo Corporation) having an outer diameter of 2 mm was inserted into and pulled off from the valve body of the sheath after the electron beam sterilization. Thereafter, the sliding resistance was measured when a catheter (produced by Terumo Corporation, Heartcath) having an outer diameter of 1.7 mm was inserted and when the catheter was pulled off.

In this instance, a maximum load when the Autograph (produced by Shimadzu Corporation, AG-IS) was used and operated at a cross head speed of 100 mm/min by 100 mm was determined.

For each of the working examples and the comparative examples, the determination was carried out with regard to five samples, and an average value was determined.

It is to be noted that the sliding resistance upon insertion was evaluated such that, if it was lower than 150 gf, then the sliding performance was good, and the sliding resistance upon pulling off was evaluated such that, if it was lower than 200 gf, then the sliding performance was good.

[2.3] Evaluation of the Negative Pressure Resisting Property

A dilator (produced by Terumo Corporation) having an outer diameter of 2 mm was inserted into the valve body of the sheath after the electron beam sterilization, the opening at the distal end portion of the sheath was sealed, whereafter air was sucked through the side port by a syringe. Then, after this state is maintained for 5 seconds, presence or absence of inflow of air was confirmed.

As apparent from Table 1 above, with the working examples (embodying the aspects of the disclosure here), good results were obtained. In contrast, with the comparative examples, satisfactory results were not obtained.

It is to be noted that, where EOG sterilization was carried out in place of the electron beam sterilization to carry out evaluation similar to that described above, similar results to those given above were obtained.

According to the disclosure here, the sliding performance of the elongated member is improved and insertion and pulling out of the elongated member can be readily carried out, and the sealability (sealing performance) of the opening and closing section is improved. In particular, the valve body is reinforced by the ribs. Also, the ribs contact the mounting section for the valve body, and consequently, deformation of the valve body is suppressed and the sealability of the opening and closing section is improved. On the other hand, when the elongated member is pulled out from the valve body, the valve body is deformed such that the central portion of the valve body is displaced in the direction of movement of the elongated member and the projections contact (point-contact) the outer circumferential surface of the elongated member. Consequently, the contact area of the outer circumferential surface of the elongated member and the valve body decreases, and the resistance (sliding resistance) when the elongated member is pulled out from the valve body decreases. Accordingly, the sliding performance of the elongated member is improved, and the elongated member can be pulled out from the valve body quite readily. Therefore, the valve body disclosed here can be used (installed) in a sheath of an introducer for introducing an elongated medical member for use with medical care such as, for example, a catheter or a guide wire into a living organism.

The detailed description above describes a preferred embodiment and variations of the valve body and medical tool. However it is to be understood that the invention is not limited to those precise embodiment and variations described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A valve body mounted in a hub of a medical tool, the hub possessing an inner circumferential surface bounding an interior of the hub, the medical tool also including a tubular sheath extending distally from the hub, the tubular sheath being configured and sized for positioning in a living organism, the valve body comprising:
   a plate-shaped elastic body possessing a first face facing the interior of the hub and an oppositely facing second face, the elastic body including an opening and closing section which opens in response to insertion of an elongated medical member and closes in response to pulling out of the elongated medical member, the opening and closing section comprising:
   a first slit formed in a thickness direction of the elastic body, the first slit extending to the second face but not opening to the first face;
   a second slit formed in a thickness direction of the elastic body, the second slit extending to the first face but not opening to the second face, the second slit intersecting the first slit in an interior portion of the elastic body that is spaced from the first and second faces of the elastic body;
   two ribs on the second face of the elastic body, each rib having opposite ends, each end of one rib being adjacent to but spaced from one of the ends of the other rib so that the two ribs are spaced apart from one another and positioned in opposing relation to each other, the second slit being positioned between the two ribs, each rib possessing an arcuate outer surface in contacting engagement with the inner circumferential surface of the hub; and
   projections on the second face of the elastic body, each of the projections extending radially and being positioned between the second slit and one of the ribs.

2. The valve body mounted in a hub of a medical tool according to claim 1, wherein the valve body is configured so that upon mounting the valve body in the hub at least part of the second slit is open.

3. The valve body mounted in a hub of a medical tool according to claim 1, wherein the valve body possesses an outer periphery and is configured relative to the hub so that prior to the valve body being mounted in the hub, the outer periphery of the valve body is greater in size than the inner circumferential surface of the hub so that upon mounting the valve body in the hub the valve body is deformed and the first slit is closed.

4. The valve body mounted in a hub of a medical tool according to claim 3, wherein the first slit is open in the natural state of the valve body, the valve body is deformed when the valve body is mounted on the mounting section in such a manner as to be compressed toward the intersecting portion of the first slit and the second slit, and the first slit is thereby closed.

5. The valve body mounted in a hub of a medical tool according to claim 1, wherein the valve body is configured so that prior to being mounted in the hub, the first slit is open, a first space is formed by an inner face of the first slit, the second slit is open, a second space is formed from an inner face of the second slit, and the first space and the second space communicate with each other through the intersecting portion.

6. The valve body mounted in a hub of a medical tool according to claim 5, wherein the valve body possesses an outer periphery and is configured relative to the hub so that prior to the valve body being mounted in the hub, the outer periphery of the valve body is greater in size than the inner circumferential surface of the hub so that upon mounting the valve body in the hub the valve body is deformed in a manner causing the first slit and/or the second slit to contact each other at least at inner peripheral faces thereof in proximity of the intersecting portion so as to be closed.

7. The valve body mounted in a hub of a medical tool according to claim 5, wherein the first space and the second space have a flattened shape.

8. The valve body mounted in a hub of a medical tool according to claim 5, wherein the first space and/or the second space has a depth which gradually decreases from the intersecting portion toward a direction away from the intersecting portion.

9. The valve body mounted in a hub of a medical tool according to claim 5, wherein the first space and/or the second space has a width which gradually decreases toward the intersecting portion.

10. A valve body made of an elastic material and configured to be mounted in a mounting section, the valve body comprising an opening and closing section which opens and closes in response to insertion and pulling out of an elongated member into and from the valve body, the valve body possessing two faces facing in opposite directions, the opening and closing section comprising:
   a first slit extending to one of the two faces of the valve body in a thickness direction of the valve body but not to an other of the two faces;
   a second slit extending to the other face of the valve body in a thickness direction of the valve body but not to the one face, the second slit intersecting the first slit at a position inside the valve body;
   two ribs on the other face of the valve body, the two ribs being disposed in opposing relationship to each other, with the second slit interposed between the two ribs; and
   projections on the other face of the valve body, each of the projections being positioned between the second slit and one of the ribs.

11. The valve body according to claim 10, wherein the ribs have an arcuate shape when the valve body is seen in plan view.

12. The valve body according to claim 10, wherein the second slit possesses a straight linear shape as viewed in plan, the ribs being line-symmetric with respect to the second slit and point-symmetric with respect to an intersecting portion of the first slit and the second slit as viewed in plan.

13. The valve body according to claim 10, wherein the ribs are spaced from an extension line of the second slit which passes through ends of the second slit.

14. The valve body according to claim 10, wherein the projections extend radially with respect to an intersecting portion of the first slit and the second slit.

15. The valve body according to claim 10, wherein each of the projections possesses one end positioned closest to an intersecting portion of the first slit and the second slit, the one end of each projection being spaced from the intersecting portion by a common distance.

16. The valve body according to claim 10, wherein the projections each have a first end located closer to the second slit and a second end, each of the projections possessing a height which gradually decreases from the second end to the first end.

17. The valve body according to claim 10, wherein the projections each have a first end located closer to the second slit and a second end, each of the projections possessing a width which gradually decreases from the second end toward the first end.

18. The valve body according to claim 10, wherein each projection possesses a height lower than a height of the ribs.

19. The valve body according to claim 10, wherein the first and second slits possess a straight line shape as viewed in plan, and the first slit and the second slit intersecting each other crosswise.

20. The valve body according to claim 10, wherein the intersecting portion has a shape of a hexahedron with 12 sides, the twelve sides including eight sides which are nodal lines formed by intersection of inner faces of the first slit and the second slit, and a sum total length of the eight sides is 1.0 to 6.0 mm.

21. The valve body according to claim 10, wherein the two ribs each possess an outer surface in contacting engagement with the inner circumferential surface of the hub.

22. A combination of an elongated medical member and a valve body mounted in a hub of a medical tool, the hub possessing an interior bounded by an inner circumferential surface, the medical tool also including a tubular sheath extending distally from the hub, the tubular sheath being configured and sized for positioning in a living organism, the valve body comprising:
- a circular elastic body possessing a first face facing the interior of the hub and a second face facing outwardly away from the interior of the hub;
- a first slit and a second slit through which the elongated medical member is insertable, the first and second slits being openable in response to insertion of the elongated medical member into the first and second slits, and closable in response to pulling out the elongated medical member from the first and second slits;
- the first slit extending into the valve body in a thickness direction of the elastic body, the first slit opening to the second face of the elastic body but not opening to the first face of the elastic body;
- the second slit extending into the valve body in the thickness direction of the elastic body, the second slit opening to the first face of the elastic body but not opening to the second face of the elastic body, the second slit intersecting the first slit in an interior portion of the elastic body that is spaced from the first and second faces of the elastic body, the second slit being elongated in a direction of elongation, the second slit having ends spaced apart in the direction of elongation;
- first and second ribs on the second face of the elastic body, the first rib having opposite ends both spaced from the second rib, the second rib having opposite ends both spaced from the first rib, the first and second ribs being spaced from an extension line of the second slit which extends in the direction of elongation and passes through ends of the second slit.
- the first and second ribs each possessing an arcuate outer surface in contacting engagement with the inner circumferential surface of the hub;
- a plurality of first projections on the second face of the elastic body, each of the first projections extending radially and being positioned between the second slit and one of the ribs; and
- a plurality of second projections on the first face of the elastic body, each of the second projections extending radially and being spaced from the first slit.

23. The valve body mounted in a hub of a medical tool according to claim 22, wherein the first slit is open in the natural state of the valve body, the valve body is deformed when the valve body is mounted on the mounting section in such a manner as to be compressed toward the intersecting portion of the first slit and the second slit, and the first slit is thereby closed.

\* \* \* \* \*